United States Patent [19]

Trummlitz et al.

[11] 4,137,313
[45] Jan. 30, 1979

[54] 2,5-DIHYDRO-1,2-THIAZINO(5,6-b)INDOLE-3-CARBOXAMIDE-1,1-DIOXIDES AND SALTS THEREOF

[75] Inventors: Günter Trummlitz; Wolfhard Engel; Ernst Seeger; Walter Haarmann; Günther Engelhardt, all of Biberach, Fed. Rep. of Germany

[73] Assignee: Boehringer Ingelheim GmbH, Ingelheim am Rhein, Fed. Rep. of Germany

[21] Appl. No.: 872,889

[22] Filed: Jan. 27, 1978

[30] Foreign Application Priority Data

Feb. 3, 1977 [DE] Fed. Rep. of Germany ....... 2704485

[51] Int. Cl.² .................... C07D 513/04; A61K 31/38
[52] U.S. Cl. ....................................... 424/246; 544/33
[58] Field of Search .......................... 544/33; 424/246

[56] References Cited
U.S. PATENT DOCUMENTS 3,992,535  11/1976  Trummlitz et al. ................... 544/33

Primary Examiner—John M. Ford
Attorney, Agent, or Firm—Hammond & Littell

[57] ABSTRACT

Compounds of the formula

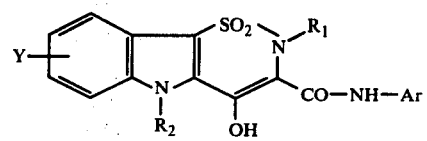

wherein
$R_1$ is hydrogen, methyl or ethyl;
$R_2$ is methyl or ethyl;
Y is hydrogen, fluorine, chlorine, bromine, methoxy, methyl, ethyl or trifluoromethyl; and
Ar is 2-thiazolyl which may have one or two methyl or ethyl substituents attached thereto; 5,6-dihydro-4H-cyclopentathiazol-2-yl; 4,5,6,7-tetrahydro-2-benzothiazolyl; 2-benzothiazolyl; 3-isothiazolyl which may have a methyl substituent attached thereto; 2-pyridyl which may have a methyl or hydroxyl substituent attached thereto; 3-pyridyl; 4-pyridyl; 4-pyrimidinyl; pyrazinyl; 2-benzimidazolyl; 2-oxazolyl which may have a methyl substituent attached thereto; 2-benzoxazolyl; or phenyl which may have a fluoro, chloro, bromo, methyl, ethyl, trifluoromethyl or methoxy substituent attached thereto; and non-toxic, pharmacologically acceptable salts thereof formed with inorganic or organic bases. The compounds as well as their salts are useful as antiphlogistics and blood platelet aggregation inhibitors.

9 Claims, No Drawings

2,5-DIHYDRO-1,2-THIAZINO(5,6-B)INDOLE-3-CARBOXAMIDE-1,1-DIOXIDES AND SALTS THEREOF

This invention relates to novel 2,5-dihydro-1,2-thiazino[5,6-b]indole-3-carboxamide-1,1-dioxides and non-toxic salts thereof, as well as to various method of preparing these compounds.

More particularly, the present invention relates to a novel class of compounds represented by the formula

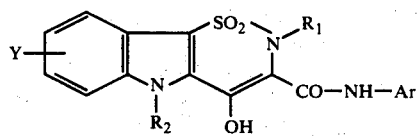

(I)

wherein
$R_1$ is hydrogen, methyl or ethyl;
$R_2$ is methyl or ethyl;
Y is hydrogen, fluorine, chlorine, bromine, methoxy, methyl, ethyl or trifluoromethyl; and
Ar is 2-thiazolyl which may have one or two methyl or ethyl substituents attached thereto; 5,6-dihydro-4H-cyclopentathiazol-2-yl; 4,5,6,7-tetrahydro-2-benzothiazolyl; 2-benzothiazolyl; 3-isothiazolyl which may have a methyl substituent attached thereto; 2-pyridyl which may have a methyl or hydroxyl substituent attached thereto; 3-pyridyl; 4-pyridyl; 4-pyrimidinyl; pyrazinyl; 2-benzimidazolyl; 2-oxazolyl which may have a methyl substituent attached thereto; 2-benzoxazolyl; or phenyl which may have a fluoro, chloro, bromo, methyl ethyl, trifluoromethyl or methoxy substituent attached thereto;
and non-toxic, pharmacologically acceptable salts thereof formed with inorganic or organic bases.

The compounds enbraced by formula I may be prepared by the following methods:

Method A

By reacting an ester of 2,5-dihydro-4-hydroxy-1,2-thiazino[5,6-b]indole-3-carboxylic acid-1,1-dioxide of the formula

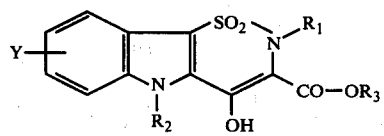

(II)

wherein
$R_1$, $R_2$ and Y have the same meanings as in formula I, and
$R_3$ is alkyl of 1 to 8 carbon atoms, aralkyl of 7 to 10 carbon atoms or phenyl,
with an aromatic amine of the formula

 $NH_2$-Ar    (III)

wherein Ar has the same meanings as in formula I.

The reaction is carried out in a suitable inert organic solvent, for example in an aromatic hydrocarbon such as benzene, toluene, xylene, chloro-benzene, o-dichlorobenzene or tetrahydronaphthalene, in dimethylformamide, dimethylacetamide or dimethylsulfoxide, in an ether such as dimethoxyethane, diethyleneglycol dimethyl ether or diphenyl ether, or also without a separate solvent in an excess of the amine. The reaction is carried out at a temperature of 60° to 200° C. Preferably, the reaction is carried out in toluene or xylene at the boiling point, where the alcohol which is formed is separated by azeotropic distillation or by heating under reflux, using a Soxhlett-extractor equipped with a molecular sieve. The pure product directly cristallizes out of the reaction mixture, or it is obtained by evaporation of the solvent or, when a water-miscible solvent is used, it is precipitated by addition of water. If 2-aminothiazole is used as the amine in the reaction, in order to avoid the decomposition of this amine, the reaction is preferably carried out in the presence of a catalytic amount of a boric acid trialkyl ester, such as boric acid tri-n-butyl ester, or of triphenylphosphine, or of a mixture of catalytic amounts of a boric acid trialkyl ester and triphenylphosphine, and/or in a nitrogen atmosphere.

Method B

Those compounds of the formula I wherein $R_1$ is methyl or ethyl, and $R_{x2}$, Y and Ar have the meanings previously defined, may also be prepared by reacting a 2,5-dihydro-4-hydroxy-1,2-thiazino[5,6-b]indole-3-carboxamide-1,1-dioxide of the formula

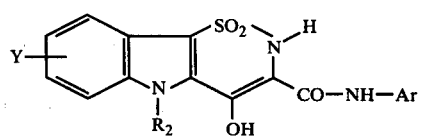

(IV)

wherein $R_2$, Y and Ar have the same meanings as in formula I, with an alkyl halide of the formula

 $R_1'$ - Hal    (V)

wherein
$R_1'$ is methyl or ethyl, and Hal is halogen,
in the presence of a base.

Examples of suitable bases are alkali metal or alkaline earth metal hydroxides, such as sodium hydroxide, potassium hydroxide or barium hydroxide; alkali metal or alkaline earth metal carbonates, such as sodium carbonate or potassium carbonate; alkali metal or alkaline earth metal alcoholates, such as sodium methylate, potassium ethylate or potassium tert. butylate; or tertiary amines; provided the reaction is carried out in an aqueous medium or in an alcoholic medium, such as in methanol, ethanol, n-propanol, isopropanol or mixtures of any two or more of these.

The alkyl halide, preferably an alkyl bromide or iodide, in alcoholic solution is added directly to the remaining components of the reaction mixture; in case methyl bromide is used, the reaction should be performed in a closed vessel.

Other suitable solvents are dimethylformamide, dimethylacetamide, dimethylsulfoxide and hexamethylphosphoric acid triamide.

If an alkali metal carbonate or alkaline earth metal carbonate is used as the base, aliphatic ketones such as acetone may also be used as solvents.

On the other hand, if the reaction is carried out in an inert organic solvent such as benzene or another aromatic hydrocarbon, or in tetrahydrofuran or another acyclic or cyclic ether, alkali metal hydrides or alkaline earth metal hydrides, such as sodium hydride, can be used as the base. In that case, the alkyl halide is added only after the reaction of the alkali metal hydride or alkaline earth metal hydride with the starting compound of the formula IV has gone to completion. The reaction temperature is from 0° to 80° C.

Method C

A compound of the formula I, wherein $R_1$ is methyl or ethyl; Ar is phenyl which may be substituted by fluorine, chlorine, bromine, methyl, ethyl, trifluoromethyl or methoxy; and wherein $R_2$ and Y have the meanings defined above, can also be prepared by reacting a 2,5-dihydro-1,2-thiazino[5,6-b]indole-4(3H)-one-1,1-dioxide of the formula

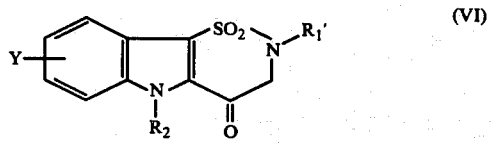

wherein $R_1'$, $R_2$ and Y have the meanings previously defined, with an isocyanate of the formula

wherein Ar' is phenyl which may have a fluoro, chloro, bromo, methyl, ethyl, trifluoromethyl or methoxy substituent attached thereto, in the presence of a base or of a Grignard reagent.

Suitable bases are tertiary amines, such as triethylamine, and 1,5-diazabicyclo[4,3-0]non-5-ene, but particularly preferred are alkali metal hydrides or alkaline earth metal hydrides, especially sodium hydride, which are used in equimolar amounts.

The reaction is advantageously performed in an inert organic solvent, for example in an aprotic organic solvent such as dimethylformamide, dimethylacetamide, dimethylsulfoxide, hexamethylphosphoric acid triamide, tetrahydrofuran, dioxane or an aromatic hydrocarbon such as benzene, at a temperature between room temperature and the boiling point of the particular solvent which is used, where the tertiary base as well as the isocyanate are preferably provided in excess over the stoichiometrically required amount.

This reaction is preferably carried out by dissolving the starting compound of the formula VI in the solvent, and then adding an equivalent amount of an alkali metal hydride or alkaline earth metal hydride and the isocyanate of the formula VII to the solution.

In those instances where a Grignard reagent, such as an alkyl magnesium halide is used, the reaction is also performed in an inert organic solvent, for example in an ether. Particularly suitable for this purpose are diethyl ether, dibutyl ether, tetrahydrofuran, anisole or mixtures of any two or more of these. The reaction temperature under these conditions is between $-20°$ and $+150°$ C., preferably between 0° and 30° C.

Method D

By reacting a 2,5-dihydro-4-hydroxy-1,2-thiazino[5,6-b]indole-3-carboxamide-1,1-dioxide of the formula

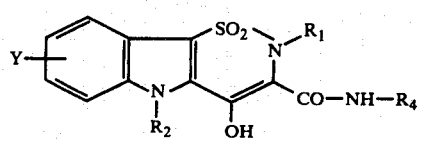

wherein
$R_1$, $R_2$ and Y have the same meanings as in formula I, and
$R_4$ is hydrogen, alkyl of 1 to 8 carbon atoms, cycloalkyl of 3 to 10 carbon atoms, aralkyl of 7 to 10 carbon atoms or phenyl,
with an aromatic amine of the formula III.

The reaction is advantageously performed in an inert organic solvent. Examples of suitable such solvents are aromatic hydrocarbons, such as benzene, toluene, xylene or o-dichloro-benzene; dimethylformamide; dimethylacetamide; dimethylsulfoxide; hexamethylphosphoric acid triamide; and ethers, such as dimethoxyethane, diethyleneglycol dimethyl ether or diphenyl ether. The reaction may, however, also be performed without a separate solvent by providing the aromatic amine reactant in sufficient excess. The reaction temperature is between 80° and 200° C.

The reaction is preferably performed in xylene at the boiling point in the presence of a catalytic amount of p-toluenesulfonic acid, and with an excess of the aromatic amine. The desired end product either crystallizes out of the reaction mixture by itself or is isolated by evaporating the solvent. If a water-miscible solvent is used, the reaction product may also be precipitated by addition of water to the reaction mixture.

Method E

A compound of the formula I wherein $R_1$ is methyl or ethyl, and $R_2$, Y and Ar have the meanings previously defined, may also be prepared by reacting an enaminecarboxylic acid halide of the formula

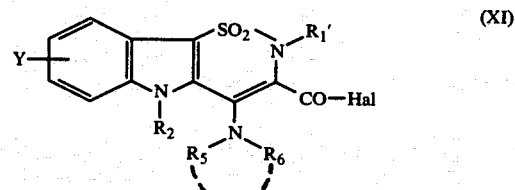

wherein
$R_1'$, $R_2$ and Y have the meanings previously defined,
Hal is halogen, preferably chlorine, and
$R_5$ and $R_6$ are each alkyl of 1 to 3 carbon atoms or, together with each other and the nitrogen atom to which they are attached, piperidino, pyrrolidino, morpholino or N'-methylpiperazino,
with an aromatic amine of the formula III, and subsequently converting the intermediate enamine-carboxamide of the formula

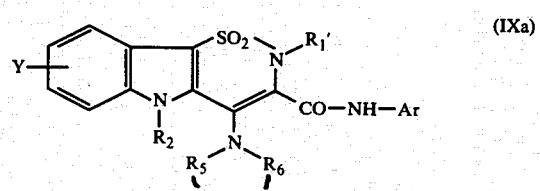

wherein $R_1'$, $R_2$, Y, Ar, $R_5$ and $R_6$ have the meanings previously defined, into the desired end product by acid hydrolysis.

The reaction of the enamine acid halide of the formula IX with the amine of the formula III is carried out in an inert organic solvent, such as an aromatic hydrocarbon or an ether, at temperatures between −40° C. and +80° C., and optionally in the presence of a tertiary organic base, such as triethylamine.

For the subsequent hydrolysis, an enamine-carboxamide of the formula IXa is heated with an aqueous or aqueous-alcoholic solution of a strong or medium strong acid, for example a hydrohalic acid, phosphoric acid, sulfuric acid, methanesulfonic acid, p-toluenesulfonic acid, trifluoroacetic acid, or mixtures of any two or more of these. Hydrohalic acids, glacial acetic acid or mixtures of acetic acid and water are preferred.

The compounds of the formula I form salts with inorganic or organic bases. Examples of non-toxic, pharmacologically acceptable salts are those formed with alkali metal alcoholates, alkali metal hydroxides, alkaline earth metal hydroxides, trialkylammonium hydroxides and alkylamines.

The starting compounds of the formula II can be obtained, for example, starting from an alkyl 3-sulfamoylindole-2-carboxylate of the formula

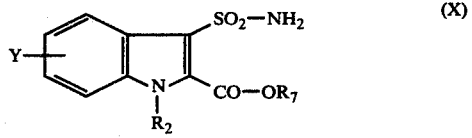

wherein
$R_2$ and Y have the meanings previously defined, and
$R_7$ is lower alkyl, such as methyl or ethyl.

For this purpose an ester of the formula X is reacted with an alcoholic alkali metal alcoholate solution, which yields an alkali metal salt of a 2H-isothiazolo[4,5-b]indole-3(4H)-one-1,1-dioxide of the formula

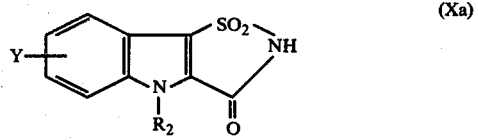

wherein $R_2$ and Y have the meanings previously defined. The alkali metal salt is then reacted with a haloacetic acid alkyl ester at a temperature of 100°–150° C. to form the corresponding ester of 3,4-dihydro-3-oxo-2H-isothiazolo[4,5-b]indole-2-acetic acid-1,1-dioxide, which is subsequently subjected to a base-catalyzed rearrangement reaction by treatment with 2 to 3 equivalents of an alkali metal alcoholate, followed by heating. After acidification of the reaction mixture, the corresponding ester of the formula II, wherein $R_1$ is hydrogen, is obtained.

The compounds of the formula II wherein $R_1$ is methyl or ethyl are obtained therefrom by alkylation with a methyl or ethyl halide in alcoholic or aqueous alcoholic solution, using one equivalent of an alkali metal hydroxide, or in an aprotic solvent, such as hexamethylphosphoric acid triamide, using one equivalent of an alkali metal hydride.

The starting compounds of the formula X wherein $R_2$ and $R_7$ are methyl, and Y is hydrogen, can be produced according to J. Szmuszkovicz [J. Org. Chem. 29, 178 (1964)]. Analoguously, the other compounds of the general formula X are obtained, starting from a known methyl or ethyl indole-2-carboxylate of the formula

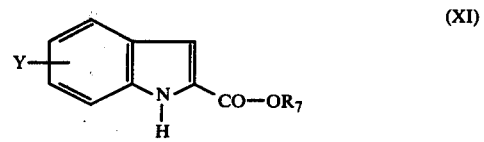

wherein $R_7$ and Y have the meanings defined above by N-alkylation with a methyl or ethyl halide in a polar aprotic solvent, such as hexamethylposphoric acid triamide, using one equivalent of an alkali metal hydride, followed by reaction with thionyl chloride and aminolysis in a mixture of ether and liquid ammonia, and subsequent oxidation with potassium permanganate in aqueous acetone. The side-products of this oxidation are 2H-isothiazolo[4,5-b]indole-3(4H)-one-1,1-dioxides of the formula Xa, which can be converted, like the carboxylates of the formula X, into esters of 3,4-dihydro-3-oxo-2H-isothiazolo[4,5-b]indole-2-acetic acid-1,1-dioxide by treatment with an alcoholic alkali metal alcoholate-solution and subsequent heating in the presence of a halo-acetate.

The starting compounds of the formula IV are obtained from an ester of 2,5-dihydro-4-hydroxy-1,2-thiazino[5,6-b]-indole-3-carboxylic acid-1,1-dioxide by reaction with an amine of the formula III according to method A.

The starting compounds of the formula VI can, for example, be obtained from an alkali metal salt of a 2H-isothiazolo[4,5-b]-indole-3(4H)-one-1,1-dioxide of the formula Xa by reaction with a halo-acetone, such as chloroacetone, in dimethylsulfoxide and at a temperature of 100° to 150° C., to form a corresponding 2-acetonyl-2H-isothiazolo[4,5-b]indol-3(4H)-one-1,1-dioxide. This compound is then subjected to a base-catalyzed rearrangement reaction in the presence of 2 to 3 equivalents of an alkali metal alcoholate, which yields a 3-acetyl-2,5-dihydro-4-hydroxy-1,2-thiazino[5,6-b]-indole-1,1-dioxide of the formula

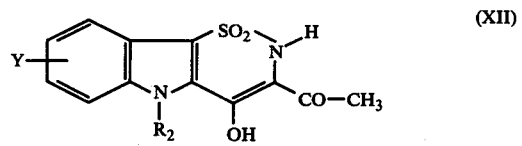

wherein $R_2$ and Y have the meanings defined above.

The acetyl derivates of the formula XII are treated in the presence of an acid and under anhydrous conditions with ethyleneglycol and form the ketals of the formula

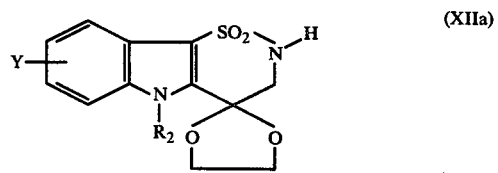

wherein $R_2$ and Y have the meanings defined above. For example, 3-acetyl-2,5-dihydro-4-hydroxy-5-methyl- 1,2-thiazino[5,6-b]indole-1,1-dioxide is refluxed with ethyleneglycol in benzene as a solvent and in the presence of p-toluenesulfonic acid as a catalyst for 5 days, which yields the ethylene ketal of 2,5-dihydro-5-methyl-1,2-thiazino[5,6-b]indole-4(3H)-one-1,1-dioxide.

The ketal of the formula XIIa is then alkylated with methyl iodide to form a compound of the formula IV wherein $R_1'$ is methyl or with ethyl iodide to obtain a compound of the formula VI wherein $R_1'$ is ethyl. The alkylation is performed in alcoholic or aqueous alcoholic solution, using one equivalent of an alkali metal hydroxide, and is followed by treatment with an acid, for example with aqueous alcoholic hydrochloric acid, whereby a 2,5-dihydro-1,2-thiazino[5,6-b]indole-4(3H)-one-1,1-dioxide of the formula VI is formed.

The starting compounds of the formula VIII can be obtained, for example, by reacting a 2,5-dihydro-1,2-thiazino[5,6-b]-indole-4(3H)-one-1,1-dioxide of the formula VI with an alkyl isocyanate, cycloalkyl isocyanate, aralkyl isocyanate or phenyl isocyanate according to method C to obtain a compound of the formula VIII where $R_4$ is alkyl, cycloalkyl, aralkyl or phenyl.

If a starting compound of the formula VIII wherein $R_4$ is hydrogen is to be obtained, an ester of 2,5-dihydro-4-hydroxy-1,2-thiazino[5,6-b]indole-3-carboxylic acid-1,1-dioxide of the formula II is reacted with ammonia.

The starting compounds of the formula IX can be obtained, for example, by reacting a 2,5-dihydro-1,2-thiazino[5,6-b]indole-4(3H)-one-1,1-dioxide of the formula VI with a secondary aliphatic amine of the formula

wherein $R_5$ and $R_6$ have the meanings defined above, in an inert organic solvent, such as benzene or toluene, and optionally in the presence of an acid catalyst, such as p-toluenesulfonic acid, to form a compound of the formula

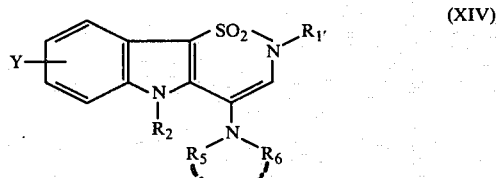

wherein $R_1'$, $R_2$, $R_5$, $R_6$ and Y have the meanings defined above, which is subsequently treated with phosgene, preferably in the presence of a tertiary organic base such as triethylamine, in an inert organic solvent such as tetrahydrofuran, at temperatures between $-50°$ C. and $+50°$ C. The enamine-carboxylic acid chloride of the formula IX is preferably used in method E without prior isolation.

The following examples illustrate the present invention and will enable others skilled in the art to understand it more completely. It should be understood, however, that the invention is not limited solletly to the particular examples given below.

EXAMPLE 1

2,5-Dihydro-2,5-dimethyl-4-hydroxy-N-(2-thiazolyl)-1,2-thiazino-[5,6-b]indole-3-carboxamide-1,1-dioxide by method A 3.2 gm (10 millimols) of methyl 2,5-dihydro-2,5-dimethyl-4-hydroxy-1,2-thiazino[5,6-b]indole-3-carboxyate-1,1-dioxide and 1.2 gm (12 millimols) of 2-amino-thiazole were refluxed in 150 ml of xylene for 5 hours in a nitrogen atmosphere. The methanol released by the reaction was separated by means of a 4-A-molecular sieve mounted in a Soxhlett-attachment. After cooling and standing overnight, the crystals which had precipitated were filtered off and washed with ether. Yield: 3.6 gm (92% of theory) of 2,5-dihydro-2,5-dimethyl-4-hydroxy-N-(2-thiazolyl)-1,2-thiazino [5,6-b]indole-3-carboxamide-1,1-dioxide of the formula

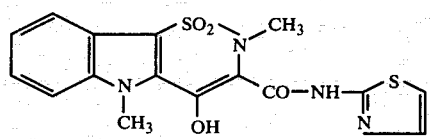

which had a melting point of 260°–261° C. (decomp.). 1H-NMR ([$D_6$]-DMSO): $\delta$ = 8.0–7.1 (m, 6, 6-H to 9-H, 4'-H, 5'-H); 4.17 (s,3, 5-$CH_3$); 2.94 (s, 3, 2-$CH_3$).

Elemental analysis: $C_{16}H_{14}N_4O_4S_2$ (390.44): Calc.: C-49.22%; H-3.55%; N-14.42%; S-16.43% Found: C-49.20%; H-3.61%; N-14.35%; S-16.65%. The starting compound was obtained by the following reaction sequence:

(a) 53.66gm (0.2 mol) of methyl 1-methyl-3-sulfamoyl-indole-2-carboxylate were added to a solution of 4.6 gm (0.2 gm-atoms) of sodium in 250 ml of absolute methanol. The reaction mixture was refluxed for 1 hour and, after cooling, the precipitate was filtered off, the filtrate was evaporated and the residue was again suction-filtered. The solid material (4-methyl-2H-isothiazolo [4,5-b]indole-3(4H)-one-1,1-dioxide sodium salt) was washed with ether several times and dried (51 gm). Then, this intermediate product was added to 100 ml of dry dimethylsulfoxide, 26 gm (0.24 mol) of methyl chloro-acetate were added, and the mixture was stirred for 1 hour at room temperature and then heated for 1 hour on an oilbath at 130° C. After cooling, a solution of 50 gm of sodium acetate in 500 ml of water was added to the reaction mixture. The precipitate was suction-filtered off, washed with ice water and with a small quantity of ice-cold methanol and with ether, and dried. Yield: 56.6 gm (91% of theory) of methyl 3,4-dihydro-4-methyl-3-oxo-2H-isothiazolo[4,5-b]indole-2-acetate-1,1-dioxide; M.p.: 220°–221° C. (from benzene).

Elemental analysis: $C_{13}H_{12}N_2O_5S$ (308.32): Calc.: C-50.64%; H-3.92%; N-9.09%; S-10.40% Found: C-50.50%; H-3.87%; N-9.31%; S-10.47%. (b) 40 ml of dry tert. butanol were added to a well-stirred suspension of 30.8 gm (0.10 mol) of methyl 3,4-dihydro-4-methyl-3-oxo-2H-isothiazolo[4,5-b]indole-2-acetate 1,1-dioxide and 16.2 gm (0.30 mol) of sodium methylate in 350 ml of dry toluene, whereby the temperature rose to 35°–40° C. and the reaction mixture turned orange. After 30 minutes of stirring the reaction mixture was heated on an oil bath at 60° C. for 2 hours. Subsequently, 100 ml of ice water were stirred into the cooled reaction mixture. The separated aqueous phase was acidified to pH 3–4 with hydrochloric acid, and the precipitate formed thereby was filtered off, washed with ice water, ice-cold methanol and ether, and dried in vacuo. Yield: 23.4 gm (76% of theory) of methyl 2,5-dihydro-4-hydroxy- 5-methyl-1,2-thiazino[5,6-b]indole-3-carboxylate-1-1-dioxide; M.p.: 213°–215° C. (from ethyl acetate).

Elemental analysis: $C_{13}H_{12}N_2O_5S$ (308.32): Calc.: C-50.64%; H-3.92%; N-9.09%; S-10.40% Found: C-50.40%; H-4.00%; N-9.00%; S-10.66%. (c) 130 ml of 1 N sodium hydroxide were added to a suspension of 40.0 gm (0.13 mol) of methyl 2,5-dihydro-4-hydroxy-5-methyl-1,-1,2-thiazino[5,6-b]indole-3-carboxylate-1,1-dioxide and 56.8 gm (0.40 mol) of methyl iodide in 400 ml of methanol, and the mixture was stirred for 24 hours at room temperature. After cooling to 0° C., the precipitate was filtered off, washed with ice water and ice-cold methanol, and dried in vacuo: 24.8 gm. The mother liquor was evaporated in vacuo to 200 ml, adjusted to pH 5 with hydrochloric acid, and admixed with 100 ml of water. After filtering off the precipitate and washing and drying it, another 9.5 gm were obtained. Both fractions were recrystallized from methanol/ethylene-chloride to yield 31.0 gm (74% of theory) of methyl 2,5-dihydro-2,5-dimethyl-4-hydroxy-1,2-thiazino[5,6-b]indole-3-carboxylate-1,1-dioxide; M.p.: 189°–190° C. 1 H-NMR ([$D_6$]-DMSO): $\int$ = 12.5 (s, 1, OH), 8.0 (m, 1) and 7.6–7.3 (m, 3; arom. H); 4.13 (s, 3, 5-$CH_3$); 3.97 (s, 3, $OCH_3$); 3.03 (s, 3, 2-$CH_3$);

Elemental analysis: $C_{14}H_{14}N_2O_5S$ (322.35): Calc.: C-52.16%; H-4.38%; N-8.69%; S-9.95% Found: C-52.20%; H-4.31%; N-8.64%; S-9.86%.

EXAMPLE 2

2,5-Dihydro-2,5-dimethyl-4-hydroxy-N-(4-methyl-2-thiazolyl)-1, 2-thiazino[5,6-b]indole-3-carboxamide-1,1-dioxide was prepared analogous to Example 1 from methyl 2,5-Dihydro-2,5-dimethyl-4-hydroxy-1,2-thiazino[5,6-b]indole-3-carboxylate 1,1-dioxide and 2-amino-4-methyl-thiazole with a yield of 88% of theory; M.p.: 270° C. (decomposition).

Elemental analysis: $C_{17}H_{16}N_4O_4S_2$ (404.47): Calc.: C-50.48%; H-3.99%; N-13.85%; S-15.86% Found: C-50.50%; H-3.99%; N-14.00%; S-16.05%.

EXAMPLE 3

2,5-Dihydro-2,5-dimethyl-4-hydroxy-N-(5-methyl-2-thiazolyl)-1,2-thiazino[5,6-b]indole-3-carboxamide-1,1-dioxide was prepared analogous to Example 1 from methyl 2,5-Dihydro-2, 5-dimethyl-4-hydroxy-1,2-thiazino[5,6-b]indole-3-carboxylate 1,1-dioxide and 2-amino-5-methyl-thiazole with a yield of 90% of theory; M.p.: 250° C. (decomposition).

Elemental analysis: $C_{17}H_{16}N_4O_4S_2$ (404.47): Calc.: C-50.48%; H-3.99%; N-13.85%; S-15.86% Found: C-50.40%; H-3.91%; N-31.71%; S-16.08%.

EXAMPLE 4

2,5-Dihydro-2,5-dimethyl-N-(4,5-dimethyl-2-thiazolyl)-4-hydroxy-1,2-thiazino[5,6-b]indole-3-carboxamide-1,1-dioxide was prepared analogous to Example 1 from methyl 2,5-Dihydro-2,5-dimethyl-4-hydroxy-1,2-thiazino[5,6-b]indol-3-carboxylate 1,1-dioxide and 2-amino-4,5-dimethyl-thiazole with a yield of 87% of theory; M.p. 265° C. (decomposition).

Elemental analysis: $C_{18}H_{18}N_4O_4S_2$ (418.51): Calc.: C-51.66% H-4.34%; N-13.39%; S-15.32% Found: C-51.50%; H-4.42%; N-13.72%; N-15.17%.

EXAMPLE 5

Analogous to Example 1, the following additional compounds were prepared from methyl 2,5-dihydro-2,5-dimethyl-4-hydroxy-1,2-thiazino[5,6-b]indole-3-carboxylate-1,1-dioxide and (a) 2-amino 4-ethyl-thiazole, (b) 2-amino-5-ethyl-thiazole (c) 2-amino-4-ethyl-5-methyl-thiazole, (d) 2-amino-5-ethyl-4-methyl-thiazole, (e) 2-amino-5,6-dihydro-4H-cyclopentathiazole and (f) 2-amino-4,5,6,7-tetrahydro-benzothiazole, respectively:

(a) N-(4-ethyl-2-thiazolyl)-2,5-dihydro-2,5-dimethyl-4-hydroxy-1,2-thiazino[5,6-b]indole-3-carboxamide-1,1-dioxide; Yield: 83% of theory;

(b) N-(5-ethyl-2-thiazolyl)-2,5-dihydro-2,5-dimethyl-4-hydroxy-1,2-thiazino[5,6-b]indole-3-carboxamide-1,1-dioxide; Yield: 95% of theory; M.p.: 238° C. (decomposition);

(c) N-(4-ethyl-5-methyl-2-thiazolyl)-2,5-dihydro-2,5-dimethyl-4-hydroxy-1,2-thiazino[5,6-b]indole-3-carboxamide-1,1-dioxide; Yield: 88% of theory; M.p.: 236°–237° C. (decomposition);

(d) N-(5-ethyl-4-methyl-2-thiazolyl)-2,5-dihydro-2,5-dimethyl-4-hydroxy-1,2-thiazino[5,6-b]indole-3-carboxamide-1,1-dioxide; Yield: 91% of theory;

(e) 2,5-Dihydro-N-(5,6-dihydro-4H-cyclopentathiazol-2-yl)-2,5-dimethyl-4-hydroxy-1,2-thiazino[5,6-b]indole-3-carboxamide-1,1-dioxide; Yield: 87% of theory; M.p. 265° C. (decomposition);

(f) 2,5-Dihydro-2,5-dimethyl-4-hydroxy-N-(4,5,6,7-tetrahydro-2-benzothiazolyl)-1,2-thiazino[5,6-b]indole-3-carboxamide-1,1-dioxide; dimethylacetamide was used as the solvent; Yield: 94% of theory; M.p.: 254° C. (decomposition).

EXAMPLE 6

2,5-Dihydro-2,5-dimethyl-4-hydroxy-N-(2-pyridyl)-1,2-thiazino-[5,6-b]indole-3-carboxamide-1,1-dioxide by method A 3.2 gm (10 millimols) of methyl 2,5-dihydro-2,5-dimethyl-4-hydroxy-1,2-thiazino[5,6-b]indole-3-carboxylate-1,1-dioxide and 1.1 gm (12 millimols) of 2-amino-pyridine were refluxed in 200 ml of xylene for 5 hours. The methanol released by the reaction was separated by means of a 4-A-molecular sieve mounted in a Soxhlett-attachment. After cooling and standing overnight the crystals which had formed were filtered off and washed with ether. Yield: 3.4 gm (89% of theory) of 2,5-dihydro-2,5-dimethyl-4-hydroxy-N-(2-pyridyl)-1,2-thiazino[5,6-b]indole-3-carboxamide-1;1-dioxide; M.p.: 232°–233° C. (decomposition).

Elemental analysis: $C_{18}H_{16}N_4O_4S$ (384.42): Calc.: C-56.24%; H-4.19%; N-14.58%; S-8.34% Found: C-55.90%; H-4.28%; N-14.46%; S-8.29%.

EXAMPLE 7

2,5-Dihydro-2,5-dimethyl-4-hydroxy-N-(4-methyl-2-pyridyl)-1,2-thiazino[5,6-b]indole-3-carboxamide-1,1-dioxide was prepared analogous to Example 6 from methyl 2,5-dihydro-2,5-dimethyl-4-hydroxy-1,2-thiazino[5,6-b]indole-3-carboxylate-1,1-dioxide and 2-amino-4-methyl-pyridine with a yield of 91% of theory; M.p.: 250°–251° C. (decomposition).

EXAMPLE 8

2,5-Dihydro-2,5-dimethyl-4-hydroxy-N-(6-methyl-2-pyridyl)-1,2-thiazino[5,6-b]indole-3-carboxamide-1,1-dioxide was prepared analogous to Example 6 from methyl 2,5-dihydro-2,5-dimethyl-4-hydroxy-1,2-thiazino[5,6-b]indole-3-carboxylate-1,1-dioxide and 2-amino-6-methyl-pyridine with a yield of 89% of theory; M.p.: 229° C. (decomposition).

EXAMPLE 9

2,5-Dihydro-2,5-dimethyl-4-hydroxy-N-phenyl-1,2-thiazino [5,6-b]-indole-3-carboxamide-1,1-dioxide by method A 2.7 gm (8.1 millimols) of methyl 2,5-dihydro-2,5-dimethyl-4-hydroxy-1,2-thiazino[5,6-b]indole-3-carboxylate-1,1-dioxide and 0.9 gm (9.6 millimols) of aniline were refluxed in 140 ml of xylene for 4 hours. The methanol released by the reaction was separated by means of a 4-Å-molecular sieve which was mounted in a Soxhlett-attachment. After cooling and standing overnight the crystals which had formed were filtered off and washed with ether. Yield: 2.8 gm (90% of theory) of 2,5-dihydro-2,5-dimethyl-4-hydroxy-N-phenyl-1,2-thiazino [5,6-b]-indole-3-carboxamide-1,1-dioxide; M.p.: 269°–270° C. (decomposition).

Elemental analysis: $C_{19}H_{17}N_3O_4S$ (383.43): Calc.: C-59.52%; H-4.47%; N-10.96%; S-8.36%: Found: C-59.60%; H-4.62%; N-10.98%; S-8.40%.

EXAMPLE 10

Analogous to Example 9, the following additional compounds were prepared from methyl 2,5-dihydro-2,5-dimethyl-4-hydroxy-1,2-thiazino[5,6-b]-indole-3-carboxylate-1,1-dioxide and (a) 4-fluoro-aniline, (b) 3-chloro-aniline, (c) 4-bromo-aniline, (d) m-toluidine, (e) p-toluidine, (f) 3-ethyl-aniline, (g) 3-trifluoromethyl-aniline and (h) o-anisidine, respectively:

(a) 2,5-Dihydro-2,5-dimethyl-N-(4-fluoro-phenyl)-4-hydroxy-1,2-thiazino[5,6-b]indole-3-carboxamide-1,1-dioxide, where chlorobenzene was used as a solvent; Yield: 72% of theory; M.p.: 271°–272° C. (decomposition).

(b) N-(3-chloro-phenyl)-2,5-dihydro-2,5-dimethyl-4-hydroxy-1,2-thiazino[5,6-b]indole-3-carboxamide-1,1-dioxide; Yield- 87% of theory; M.p.: 275° C. (decomposition).

(c) N-(4-bromo-phenyl)-2,5-dihydro-2,5-dimethyl-4-hydroxy-1, 2-thiazino[5,6-b]indole-3-carboxamide-1,1-dioxide; Yield: 93% of theory; M.p.: 272° C. (decomposition).

(d) 2,5-Dihydro-2,5-dimethyl-4-hydroxy-N-(m-tolyl)-1,2-thiazino-[5,6-b]indole-3-carboxamide-1,1-dioxide; Yield: 97% of theory; M.p.: 250° C. (decomposition).

(e) 2,5-Dihydro-2,5-dimethyl-4-hydroxy-N-(p-tolyl)-1,2-thiazino[5,6-b]indole-3-carboxamide-1,1-dioxide, where o-dichlorobenzene was used as a solvent; Yield: 72% of theory; M.p.: 267° C. (decomposition).

(f) N-(3-ethylphenyl)-2,5-dihydro-2,5-dimethyl-4-hydroxy-1,2-thiazino[5,6-b]indole-3-carboxamide-1,1-dioxide; Yield: 81% of theory.

(g) 2,5-Dihydro-2,5-dimethyl-4-hydroxy-N-(3-trifluoromethylphenyl)-1,2-thiazino[5,6-b]indole-3-carboxamide-1,1-dioxide, where diethyleneglycol dimethyl ether was used as a solvent; Yield: 70% of theory; M.p.: 233° C. (decomposition).

(h) 2,5-Dihydro-2,5-dimethyl-4-hydroxy-N-(2-methoxy-phenyl)-1,2-thiazino[5,6-b]indole-3-carboxamide-1,1-dioxide; Yield: 98% of theory; M.p.: 230° C. (decomposition).

EXAMPLE 11

N-(2-benzothiazolyl)-2,5-dihydro-2,5-dimethyl-4-hydroxy-1,2-thiazino[5,6-b]indole-3-carboxamide-1,1-dioxide by method A 1.0 gm (3.1 millimols) of methyl 2,5-dihydro-2,5-dimethyl-4-hydroxy-1,2-thiazino[5,6-b]indole-3-carboxylate-1,1-dioxide and 0.46 gm (3.1 millimols) of 2-amino-benzothiazole were refluxed in 50 ml of xylene for 5 hours. 1.1 gm (81% of theory) of N-(2-benzothiazolyl)-2,5-dihydro-2,5-dimethyl-4-hydroxy-1,2-thiazino[5,6-b]-indole-3-carboxamide-1,1-dioxide crystallized out of the hot reaction mixture. M.p.: 258° C. (decomposition).

EXAMPLE 12

2,5-Dihydro-4-hydroxy-5-methyl-N-(2-thiazolyl)-1,2-thiazino-[5,6-b]indole-3-carboxamide-1,1-dioxide by method A 3.0 gm (9.7 millimols) of methyl 2,5-dihydro-4-hydroxy-5-methyl-1,2-thiazino-[5,6-b]indole-3-carboxylate-1,1-dioxide, 1.0 gm-(10 millimols) of 2-aminothiazole and 150 ml of xylene were refluxed for 3.5 hours in a Soxhlett-apparatus filled with a 4-Å-molecular sieve. The reaction mixture then was filtered and yielded 2.2 gm (63% of theory) of crystalline 2,5-dihydro-4-hydroxy-5-methyl-N-(2-thiazolyl)-1,2-thiazino[5,6-b]indole-3-carboxamide-1,1-dioxide; M.p.: 260° C. (decomposition).

EXAMPLE 13

2,5-Dihydro-4-hydroxy-5-methyl-N-phenyl-1,2-thiazino[5,6-b]-indole-3-carboxamide-1,1-dioxide was prepared analogous to Example 12 from methyl 2,5-dihydro-4-hydroxy-5-methyl-1,2-thiazino [5,6-b]indole-3-carboxylate-1,1-dioxide and aniline with a 86% yield; M.p.: 252° C. (decomposition).

EXAMPLE 14

2-Ethyl-2,5-dihydro-4-hydroxy-5-methyl-N-(2-thiazolyl)-1,2-thiazino[5,6-b]indole-3-carboxamide-1,1-dioxide by method A 1.7 gm (5 millimols) of methyl 2-ethyl-2,5-dihydro-4-hydroxy-5-methyl-1,2-thiazino[5,6-b]indole-3-carboxylate-1,1-dioxide and 0.5 gm (5 millimols) of 2-aminothiazol were refluxed in 100 ml of xylene for 6 hours. Then, the hot reaction mixture was filtered. After cooling, 1.2 gm (59% of theory) of 2-ethyl-2,5-dihydro-4-hydroxy-5-methyl-N-(2-thiazolyl)-1,2-thiazino[5,6-b]indole-3-carboxamide-1,1-dioxide crystallized out of the filtrate; M.p.: 224–225° C. (decomposition). The starting compound was obtained as follows: 0.87 gm of 55% dispersion of sodium hydride in oil (20 millimols) was added in small portions to a cooled suspension of 6.2 gm (20 millimols) of methyl 2,5-dihydro-4-hydroxy-5-methyl-1,2-thiazino [5,6-b]indole-3-carboxylate-1,1-dioxide in 75 ml of hexamethyl-phosphoric acid triamide. After stirring for 1.5 hours at room temperature, 10 ml (0.124 mols) of ethyl iodide were added dropwise to the reaction mixture, while cooling. After another 18 hours of stirring at room temperature, 200 ml of ice water were added to the mixture. Then, the mixture was extracted with ether several times, and the combined ether phases were washed with water several times, dried and evaporated in vacuo. The solid residue was treated with a small quantity of cool methanol, filtered and washed with methanol. After recrystallization from methanol-/ethylene chloride, 1.9 gm (28% of theory) of methyl 2-ethyl-2,5-dihydro-4-hydroxy-5-methyl-1,2-thiazino [5,6-b]indole-3-carboxylate-1,1-dioxide were obtained, M.P.: 184° C.

EXAMPLE 15

5-Ethyl-2,5-dihydro-4-hydroxy-2-methyl-N-(2-thiazolyl)-1,2-thiazino[5,6-b]indole-3-carboxamide-1,1-dioxide by method A 1.5 gm (45 millimols) of methyl 5-ethyl-2,5-dihydro-4-hydroxy-2-methyl-1,2-thiazino[5,6-b]indole-3-carboxylate-1,1-dioxide, 0.5 gm (5 millimols) of 2-aminothiazole and 0.1 mgm of tri-n-butylborate were refluxed in 120 ml of xylene for 6 hours. The hot reaction mixture was then filtered, and 0.9 gm of raw product crystallized out of the filtrate. After evaporating the mother liquor, another 0.9 gm of raw product was obtained. After recrystallizing both fractions from ethylene chloride 1.3 gm (71% of theory) of 5-ethyl-2,5-dihydro-4-hydroxy-2-methyl-N-(2-thiazolyl)-1,2-thiazino [5,6-b]indole-3-carboxamide-1,1-dioxide were obtained; M.p.: 230° C. (decomposition).

Elemental analysis: $C_{17}H_{16}N_4O_4S_2$ (404.48): Calc.: C-50.48; H-3.99%; N-13.85%; S-15.84%: Found: C-50.20%; H-4.13%; N-13.50%; S-15.90%. The starting compound was obtained by the following reaction sequence:

(a) Over a period of 2 hours 6.2 gm of a 55% dispersion of sodium hydride in oil (0.14 mol) were added, while vigorously stirring, to a solution of 25.0 gm (0.13 mol) of methyl indole-2-carboxylate in 100 ml of hexamethylphosphoric acid triamide at a temperature of 0° C. Subsequently, the reaction mixture was stirred for 3 hours at room temperature. 20.6 gm (0.13 mol) of ethyl iodide were then added dropwise to the reaction mixture, which had been recooled to 0° C., in a way such that the reaction temperature did not rise above 25° C. After 10 hours of stirring, 500 ml of ice water were added to the reaction mixture while stirring and cooling, and the aqueous mixture was extracted 5 times with ether. The combined ether extracts were washed with water, treated with activated charcoal, dried over magnesium sulfate and evaporated. The pure product thus obtained (26 gm) was then distilled in a fine vacuum (0.015 mm). The oil distilling over at 77°–78° C. was ethyl 1-ethyl-indole-2-carboxylate; Yield: 25.5 gm (90% of theory). (b) 60 ml of thionyl chloride were added all at once to 25 gm (0.115 mol) of ethyl 1-ethyl-indole-2-carboxylate in a 500 ml round-bottom flask equipped with a gas vent while vigorously stirring. After the evolution of gas had ceased, the reaction mixture was evaporated in vacuo at 30° C. The residue was suspended in a small quantity of dry ether, the suspension was suction-filtered, and the filter cake was immediately added in small portions to a solution of 200 ml of condensed ammonia in 500 ml of dry ether at −60° C. The temperature rose to −40° C. Then, the reaction mixture was allowed to warm to room temperature over a period of 6 hours, and was then stirred for another 12 hours. Thereafter, the mixture was admixed with water and additional ether. The ether phase then was washed with water, dried and evaporated in vacuo.

The raw product thus obtained was recrystallized from petroleum ether (b.p. 60°–80° C.). Yield 28.6 gm (89% of theory) of ethyl 1-ethyl-3-aminosulfinyl-indole-carboxylate; M.p.: 78°–80° C.

(c) Ethyl 1-ethyl-3-sulfamoyl-indole-2-carboxylate and 4-ethyl-2H-isothiazolo[4,5-b]indole-3(4H)-one-1,1-dioxide A solution of 15.8 gm (0.10 mol) of potassium permanganate in 400 ml of water was added dropwise to a solution of 28.0 gm (0.10 mol) of ethyl 1-ethyl-3-aminosulfinyl-indole-carboxylate in 1 liter of acetone, while externally cooling, so that a reaction temperature of 20°–23° C. was maintained. Subsequently, the mixture was stirred for 20 hours. The precipitated manganese dioxide was filtered off and washed with water and acetone, and the combined filtrates were evaporated in vacuo at 30° C. to about 250 ml.

The precipitate formed thereby was filtered off, washed well with water and dried in vacuo. 20.7 gm (70% of theory) of ethyl 1-ethyl-3-sulfamoyl-indole-2-carboxylate were obtained; M.p.: 148°–149° C.

After acidification with 5 N hydrochloric acid, another precipitate was separated from the filtrate, washed and dried, yielding 6.0 gm (24% of theory) of 4-ethyl-2H-isothiazolo[4,5-b]indole-3(4H)-one-1,1-dioxide.

(d) Methyl 4-ethyl-3,4-dihydro-3-oxo-2H-isothiazolo[4,5-b]indole-2-acetate-1,1-dioxide (α) From ethyl 1-ethyl-3-sulfamoyl-indole-2-carboxylate 29.6 gm (0.1 mol) of ethyl 1-ethyl-3-sulfamoylindole-2-carboxylate were added to a solution of 2.3 gm of sodium (0.1 gm-atom) in 150 ml of methanol. Subsequently, the mixture was refluxed for 1 hour and afterwards evaporated to dryness. The residue was suspended in 250 ml of ether, the suspension was suction-filtered, the filter cake was dried and suspended in 40 ml of dimethylsulfoxide, and the suspension was admixed with 10.5 ml (0.12 mol) of methyl chloroacetate. The reaction mixture was then heated at 130° C. for one hour and then, after cooling, admixed with a solution of 10 gm of sodium acetate in 150 ml of water. The precipitate formed thereby was suction-filtered off and recrystallized from carbon tetrachloride/ethylene chloride. Yield: 19.5 gm (60.5% of theory) of methyl 4-ethyl-3,4-dihydro-3-oxo-2H-isothiazolo[4,5-b]indole-2-acetate-1,1-dioxide; M.p.: 176° C.

(β) from 4-ethyl-2H-isothiazolo[4,5-b]indole-3(4H)-one-1,1-dioxide

Analogous to (α) above, 5.0 gm (20 millimols) of 4-ethyl-2H-isothiazolo[4,5-b]indole-3(4H)-one-1,1-dioxide were reacted with sodium methylate and methyl chloracetate, yielding, 4.0 gm (62% of theory) of methyl 4-ethyl-3,4-dihydro-3-oxo-2H-isothiazolo[4,5-b]indole-2-acetate-1,1-dioxide; M.p.: 176° C.

(e) 19.3 gm (60 millimols) of methyl 4-ethyl-3,4-dihydro-3-oxo-2H-isothiazolo[4,5-b]indole-2-acetate-1,1-dioxide and a suspension of 9.7 gm (180 millimols) of sodium methylate in 150 ml of toluene were admixed, while vigorously stirring, with 30 ml of dry tert. butanol, and the mixture was stirred for 30 minutes at room temperature and then for 90 minutes at 60° C. Subsequently, the reaction mixture was cooled on an ice bath and admixed with 120 ml of ice water. The organic phase was extracted with water, and the aqueous phase was extracted with ether. The combined aqueous phases were then acidified with hydrochloric acid to pH 3. The precipitate formed thereby was washed with water, methanol and ether, and after recrystallization from ethylene chloride yielded 8.3 gm (43% of theory) of methyl 5-ethyl-2,5-dihydro-4-hydroxy-1,2-thiazino-[5,6-b]indole-3-carboxylate 1,1-dioxide; M.p.: 216° C. (decomposition).

(f) 8.1 gm (25 millimols) of methyl 5-ethyl-2,5-dihydro-4-hydroxy-1,2-thiazino-[5,6-b]indole-3-carboxylate 1,1-dioxide and a suspension of 10.7 gm (75 millimols) of methyl iodide in 150 ml of methanol were admixed with a solution of 1 gm (25 millimols) of sodium hydroxide in 30 ml of water. After 24 hours of stirring at room temperature, the precipitate which had formed was filtered off, washed and dried. Yield: 4.9 gm (58% of theory) of methyl 5-ethyl-2,5-dihydro-4-hydroxy-2-methyl-1,2-thiazino[5,6-b]indole-3-carboxylate 1,1-dioxide; M.p.: 154° C.

EXAMPLE 16

5-Ethyl-2,5-dihydro-4-hydroxy-2-methyl-N-(2-pyridyl)-1,2 thiazino[5,6-b]indole-3-carboxamide 1,1-dioxide was prepared analogous to Example 15 from methyl 5-ethyl-2,5-dihydro-4-hydroxy-2-methyl-1,2-thiazino[5,6-b]indole-3-carboxylate-1,1-dioxide and 2-amino-pyridine with a yield of 72% of theory. M.p.: 232° C. (decomposition, from xylene).

EXAMPLE 17

5-Ethyl-2,5-dihydro-4-hydroxy-2-methyl-N-phenyl-1,2-thiazino-[5,6-b]indole-3-carboxamide-1,1-dioxide was prepared analogous to Example 15 from methyl 5-ethyl-2,5-dihydro-4-hydroxy-2-methyl-1,2-thiazino[5,6-b]indole-3-carboxylate-1,1-dioxide and aniline a yield of 56% of theory. M.p.: 268° C. (decomposition; from xylene).

EXAMPLE 18

8-Chloro-2,5-dihydro-2,5-dimethyl-4-hydroxy-N-(2-thiazolyl)-1,2-thiazino[5,6-b]indole-3-carboxamide-1,1-dioxide by method A 3.0 gm (8.4 millimols) of methyl 8-chloro-2,5-dihydro-2,5-dimethyl-4-hydroxy-1,2-thiazino[5,6-b]indole-3-carboxylate 1,1-dioxide, 0.9 gm (9 millimols) of 2-amino-thiazole and 50 mgm of tri-n-butyl borate were refluxed in 300 ml of dry xylene for 6 hours. The methanol released by the reaction was separated by means of a 4-Å-molecular sieve in a Soxhlet-attachment. 3.1 gm of crystals were separated from the cooled reaction mixture by filtration and subsequently boiled in a mixture of 100 ml of acetonitrile and 1 ml of glacial acetic acid. After filtration and drying, 2.5 gm (68% of theory) of 8-chloro-2,5-dihydro-2,5-dimethyl-4-hydroxy-N-(2-thiazolyl)-1,2-thiazino[5,6-b]indole-3-carboxamide-1,1-dioxide were obtained; M.p.: 282° C. (decomposition).

Elemental analysis: $C_{16}H_{13}ClN_4O_4S_2$ (424.89): Calc. C-45.23%; H-3.08%; CL-8.35%; H-13.19%; S-15.09%: Found: C-45.30%; H-3.03%; Cl-8.44%; H-12.97%; S-14.93%.

The starting compound was obtained by the following reaction sequence:

(a) 8.7 gm (0.2 mol) of a 55% dispersion of sodium hydride in oil were added over a period of 15 minutes at a temperature of 0° C. and in a nitrogen atmosphere to a solution of 40.0 gm (0.18 mol) of ethyl 5-chloro-indole-2-carboxylate in 150 ml of hexamethyl-phosphoric acid triamide. After stirring the resulting mixture for 2.5 hours at room temperature, 35.5 gm (0.25mol) of methyl iodide were added dropwise, while cooling. After stirring overnight, 1200 ml of ice water were added to the mixture, while externally cooling on an ice bath. The aqueous mixture was then extracted 5 times with 150 ml of ether each. The combined ether extracts were washed with water 5 times, dried over magnesium sulfate, and evaporated in vacuo. The raw product was then recrystallized from petroleum ether, yielding 35.8 gm (85% of theory) of ethyl 5-chloro-1-methyl-indole-2-carboxylate. M.p.: 81.5°–82° C.

(b) 75 ml of thionyl chloride were added to 35.7 gm (0.15 mols) of ethyl 5-chloro-1-methyl-indole-2-carboxylate, while vigorously stirring. After 30 minutes of stirring at room temperature, 60 ml of ether were added. The precipitate formed thereby (ethyl 5-chloro-3-chlorosulfinyl-1-methyl-indole-2-carboxylate) was filtered off, washed with ether, and added in small portions to a solution of 200 ml of condensed ammonia in 500 ml of ether at −60° C. After stirring of the reaction mixture for 1 hour at −60° C., the temperature was slowly allowed to rise to +20° C., and then stirring was continued overnight. After addition of 150 ml of water the precipitate formed thereby was filtered off, washed with water and ether, and dried. Yield: 39 gm (86% of theory) of ethyl 3-aminosulfinyl-5-chloro-1-methyl-indole-2-carboxylate; M.p.: 144° C. (decomposition).

(c) A solution of 15.8 gm (0.1 mols) of potassium permanganate in 300 ml of water was added dropwise over a period of 2.5 hours to a solution of 37.6 gm (0.125 mols) of ethyl 3-aminosulfinyl-5-chloro-1-methyl-indole-2-carboxylate in 2500 ml of acetone at 20° C. After stirring overnight at room temperature, the precipitate which had formed was filtered off and washed with warm water and acetone. The filtrate then was evaporated in vacuo at 25°–30° C. to a volume of about 350 ml. The crystallized product, ethyl 5-chloro-1-methyl-3-sulfamoyl-indole-2-carboxylate, was filtered off, washed with water and dried. Yield: 30.5 gm (77% of theory); M.p.: 207°–208° C. After acidification of the filtrate to pH 3, another product, 7-chloro-4-methyl-2H-isothiazolo[4,5-b]indole-3-(4H)-one-1,1-dioxide, was obtained, which was filtered off, washed with water and dried. Yield: 3.9 gm (12% of theory); M.p.: 288° C. (decomposition).

(d) 30.5 gm (0.096 mols) of ethyl 5-chloro-1-methyl-3-sulfamoyl-indole-2-carboxylate were added to a solution of 2.3 gm (0.1 gm-atom) of sodium in 200 ml of anhydrous ethanol. The reaction mixture was refluxed for 1 hour and then cooled on an ice bath. The precipitate formed thereby, the sodium salt of 7-chloro-4-methyl-2H-isothiazolo[4,5-b]indole-3(4H)-one-1,1-dioxide, was filtered off, washed with ethanol and ether, dried and subsequently dissolved in 60 ml of dry dimethylsulfoxide, and the solution was admixed with 13 gm (0.12 mols) of methyl chloroacetate. The resulting solution was heated for one hour on an oil-bath at 125° C., then cooled on an ice bath, and admixed with a solution of 50 gm of sodium acetate in 250 ml of water. The precipitate formed thereby was filtered off, washed with ice water, ice-cold methanol and ether, and dried. Yield: 26.1 gm (79% of theory) of methyl 7-chloro-3,4-dihydro-4-methyl-3-oxo-2H-isothiazolo[4,5-b]indole-2-acetate-1,1-dioxide; M.p.: 271°–272° C.

(e) 25 ml of anhydrous tert. butanol were added to a well-stirred suspension of 26 gm (76 millimols) of methyl 7-chloro-3,4-dihydro-4-methyl-3-oxo-2H-isothiazolo[4,5-b]indole-2-carboxylate 1,1-dioxide and 12.3 gm (228 millimols) of sodium methylate in 200 ml of anhydrous toluene, whereby the temperature rose by about 15° C. and the reaction mixture turned orange. After 45 minutes of stirring at room temperature the mixture was heated on an oil bath at 60° C. for 1.5 hours. Subsequently, 100 ml of ice water were stirred into the cooled reaction mixture. The aqueous phase was separated and acidified to pH 3-4 with hydrochloric acid. The precipitate formed thereby was filtered off, and washed with ice water, ice-cold methanol and ether. Yield: 14.1 gm (54% of theory) of methyl 8-chloro-2,5-dihydro-4-hydroxy-5-methyl-1,2-thiazino[5,6-b]indole-3-carboxylate 1,1-dioxide; M.p.: 258° C. (decomposition).

(f) A solution of 1.7 gm (42 millimols) of sodium hydroxide in 50 ml of water was added dropwise to a suspension of 13.8 gm (40 millimols) of methyl 8-chloro-2,5-dihydro-4-hydroxy-5-methyl-1,2-thiazino[5,6-b]indole-3-carboxylate 1,1-dioxide and 17 gm (0.12 mol) of methyl iodide in 150 ml of methanol. After 24 hours of stirring at room temperature the reaction mixture was cooled, and the precipitate which had formed was filtered off, washed with water, ice-cold methanol and ether. Yield: 10.2 gm (71.5% of theory) of methyl 8-chloro-2,5-dihydro-2,5-dimethyl-4-hydroxy-1,2-thiazino[5,6-b]indole-3-carboxylate 1,1-dioxide; M.p.: 184° C. (decomposition).

EXAMPLE 19

8-Chloro-2,5-dihydro-2,5-dimethyl-4-hydroxy-N-(4-methyl-2-thiazolyl)-1,2-thiazino[5,6-b]indole-3-carboxamide-1,1-dioxide was prepared analogous to Example 18 from methyl 8-chloro-2,5-dihydro-2,5-dimethyl-4-hydroxy-1,2-thiazino[5,6-b]indole-3-carboxylate 1,1-dioxide and 2-amino-4-methyl-thiazole with a yield of 81% of theory.

Elemental analysis: $C_{17}H_{15}ClN_4O_4S_2$ (438.92): Calc.: C-46.52%; H-3.44%; Cl-8.08%; N-12.77%; S-14.61%: Found: C-46.40%; H-3.58%; Cl-8.01%; N-12.90%; S-14.55%.

EXAMPLE 20

8-Chloro-2,5-dihydro-2,5-dimethyl-4-hydroxy-N-(2-pyridyl)-1,2-thiazino[5,6-b]indole-3-carboxamide-1,1-dioxide was prepared analogous to Example 18 from methyl 8-chloro-2,5-dihydro-2,5-dimethyl-4-hydroxy-1,2-thiazino[5,6-b]indole-3-carboxylate-1,1-dioxide and 2-amino-pyridine with a yield of 72% of theory; M.p.: 245° C. (decomposition).

EXAMPLE 21

8-Chloro-2,5-dihydro-2,5-dimethyl-4-hydroxy-N-phenyl-1,2-thiazino[5,6-b]indole-3-carboxamide-1,1-dioxide was prepared analogous to Example 18 from methyl 8-chloro-2,5-dihydro-methyl 2,5-dimethyl-2-hydroxy-1,2-thiazino[5,6-b]indole-3-carboxylate-1,1-dioxide and aniline with a yield of 77% of theory; M.p.: 285° C. (decomposition).

EXAMPLE 22

Analogous to Example 18, the following additional compounds were prepared from (a) methyl 2,5-dihydro-2,5-dimethyl-8-fluoro-4-hydroxy-1,2-thiazino[5,6-b]indole-3-carboxylate-1,1-dioxide, (b) methyl 8-bromo-2,5-dihydro-2,5-dimethyl-4-hydroxy-1,2-thiazino[5,6-b]-indole-3-carboxylate-1,1-dioxide, (c) methyl 2,5-dihydro-2,5-dimethyl-6-fluoro-4-hydroxy-1,2-thiazino[5,6-b]indole-3-carboxylate-1,1-dioxide, (d) methyl 7-chloro-2,5-dihydro-2,5-dimethyl-4-hydroxy-1,2-thiazino[5,6-b]indole-3-carboxylate-1,1-dioxide, and (e) methyl 9-chloro-2,4-dihydro-2,5-dimethyl-4-hydroxy-1,2-thiazino[5,6-b]indole-3-carboxylate-1,1-dioxide, respectively, and 2-amino-thiazole:

(a) 2,5-Dihydro-2,5-dimethyl-8-fluoro-4-hydroxy-N-(2-thiazolyl)-1,2-thiazino[5,6-b]indole-carboxamide-1,1-dioxide; Yield: 81% of theory.

(b) 8-Bromo-2,5-dihydro-2,5-dimethyl-4-hydroxy-N-(2-thiazolyl)-1,2-thiazino[5,6-b]indole-3-carboxamide-1,1-dioxide; Yield: 76% of theory.

(c) 2,5-Dihydro-2,5-dimethyl-6-fluoro-4-hydroxy-N-(2-thiazolyl-1,2-thiazino[5,6-b]indole-carboxamide-1,1-dioxide; Yield: 87% of theory.

(d) 7-Chloro-2,5-dihydro-2,5-dimethyl-4-hydroxy-N-(2-thiazolyl)-1,2-thiazino[5,6-b]indole-3-carboxamide-1,1-dioxide; Yield: 68% of theory.

(e) 9-Chloro-2,5-dihydro-2,5-dimethyl-4-hydroxy-N-(2-thiazolyl)-1,2-thiazino[5,6-b]indole-3-carboxamide-1,1-dioxide; Yield: 83% of theory.

The starting compounds were obtained from (a) methyl 5-fluoro-indole-2-carboxylate, (b) ethyl-5-bromo-indole-2-carboxylate, (c) ethyl 7-fluoro-indole-2-carboxylate (d) ethyl 6-chloro-indole-2-carboxylate, and (e) ethyl 4-chloro-indole-2-carboxylate, respectively, by the successive reactions with methyl iodide analogous to Example 18(a), with thionylchloride and ammonia analogous to Example 18(b), with potassium permanganate analogous to Example 18(c), with sodium methylate and methyl chloroacetate analogous to Example 18(d) and finally with sodium methylate analogous to Example 18(e) and with methyl iodide analogous to Example 18(f).

EXAMPLE 23

2,5-dihydro-2,5-dimethyl-4-hydroxy-8-methoxy-N-(2-thiazolyl)-1,2-thiazino[5,6-b]indole-carboxamide-1,1-dioxide by method A 5.3 gm (0.015 mol) of methyl 2,5-dihydro-2,5-dimethyl-4-hydroxy-8-methoxy-1,2-thiazino-[5,6-b]indole-3-carboxylate, 1.6 gm (0.016 mol) of 2-amino-thiazole and 50 mgm of tri-n-butyl borate were refluxed for 5.5 hours in 500 ml of dry xylene. The methanol released by the reaction was separated by a 4-A-molecular sieve in a Soxhlett-attachment. By filtration of the hot reaction mixture, 2.4 gm of 2,5-dihydro-2,5-dimethyl-4-hydroxy-8-methoxy-N-(2-thiazolyl) 1,2-thiazino[5,6-b]indole-3-carboxamide-1,1-dioxide were obtained, and another 2.2 gm of the same compound were obtained from the filtrate after cooling and standing overnight and subsequent filtration. Yield: 73% of theory; M.p. 249° C. (decomposition).

The starting compound was obtained by the following reaction sequence:

(a) 50 gm (0.24 mol) of methyl 5-methoxy-indole-2-carboxylate were reacted with 11 gm (0.25 mol) of a 55% dispersion of sodium hydride in oil and 42.6 gm (0.3 mol) of methyl iodide analogous to Example 18(a), and the resulting product was recrystallized from methanol. Yield: 47.7 gm (90% of theory) of methyl 5-methoxy-1-indole-2-carboxylate; M.p.: 129.5°-130° C.

(b) 70 ml of thionyl chloride were poured over 30 gm (0.137 mol) of methyl 5-methoxy-1-methyl-indole-2-carboxylate in a 500 ml-flask equipped with a gas vent tube, while stirring. At once, a vigorous evolution of gas occured. After 5 minutes of stirring at room temperature, 50 ml of ether were added. After another 30 minutes, the precipitate which had formed was filtered off and washed with ether, yielding 36 gm of methyl 3-chloro-sulfinyl-5-methoxy-1-methyl-indole-carboxylate (M.p.: with decomposition at 90° C.). Another 4.8 gm of the same product were isolated from the filtrate after evaporating it in vacuo, suspending the residue in little ether, and filtering the suspension. Subsequently, the chloro-sulfinyl-compound thus obtained was immediately added to a solution of 100 ml of condensed ammonia in 400 ml of dry ether at −60° C. The subsequent reaction and processing was performed analogous to Example 18(b). 30.5 gm of methyl 3-amino-sulfinyl-5-methoxy-1-methyl-indole-2-carboxylate were obtained (79% of theory). M.p.: 149°–150° C.

(c) A suspension of 40.8 gm (0.145 mol) of methyl 3-aminosulfinyl-5-methoxy-1-methyl-indole-2-carboxylate in 3 liters of acetone was reacted with 17.4 gm (0.11 mol) of potassiumpermanganate in 350 ml of water and processed analogous to Example 18(c). 33.7 gm (78% of theory) of methyl 5-methoxy-1-methyl-3-sulfamoyl-indole-2-carboxylate, M.p.: 190° C., and 7.4 gm (19% of theory) of 7-methoxy-4-methyl-2H-isothiazolo[4,5-b]indole-3(4H)-one-1,1-dioxide, M.p.: above 290° C. (decomposition), were obtained.

(d) 33.4 gm (0.112 mol) of methyl 5-methoxy-1-methyl-3-sulfamoyl-indole-2-carboxylate were reacted analogous to Example 18(d) with sodium xethylate in ethanol to form the sodium salt of 7-methoxy-4-methyl-2H-isothiazolo[4,5-b]indole-3(4H)-one-1,1-dioxide, which was subsequently converted into methyl 3,4-dihydro-7-methoxy-4-methyl-3-oxo-2H-isothiazolo[4,5-b]indole-2-acetate-1,1-dioxide; Yield: 34.5 gm (91% of theory); M.p. 205° C.

(e) 35.1 gm (0.104 mol) of methyl 3,4-dihydro-7-methoxy-4-methyl-3-oxo-2H-isothiazolo[4,5-b]indole-2-acetate 1,1-dioxide were reacted analogous to Example 18(e) with sodium methylate in toluene/tert. butanol to form 20.6 gm (59% of theory) of methyl 2,5-dihydro-4-hydroxy-8-methoxy-5-methyl-1,2-thiazino[5,6-b]indole-3-carboxylate 1,1-dioxide; M.p.: 225°–226° C.

(f) 20.4 gm (60 millimols) of methyl 2,5-dihydro-4-hydroxy-8-methoxy-5-methyl-1,2-thiazino[5,6-b]indole-3-carboxylate 1,1-dioxide were reacted analogous to Example 18 (f) wtih a sodium hydroxide solution and methyl iodide in methanol to yield 17.9 gm (85% of theory) of methyl 2,5-dihydro-2,5-dimethyl-4-hydroxy-8-methoxy-1,2-thiazino[5,6-b]indole-3-carboxylate 1,1-dioxide; M.p.: 200°–201° C.

EXAMPLE 24

2,5-Dihydro-2,5-dimethyl-4-hydroxy-8-methoxy-N-(2-pyridyl)-1,2-thiazino[5,6-b]indole-3-carboxamide-1,1-dioxide by method A 2.1 gm (6 millimols) of methyl 2,5-dihydro-2,5-dimethyl-4-hydroxy-8-methoxy-1,2-thiazino[5,6-b]indole-3-carboxylate 1,1-dioxide and 0.66 gm (7 millimols) of 2-amino-pyridine were refluxed in 250 ml of xylene for 5.5 hours. Then, the reaction mixture was cooled and filtered. Yield: 1.9 gm (77% of theory) of 2,5-dihydro-2,5-dimethyl-4-hydroxy-8-methoxy-N-(2-pyridyl)-1,2-thiazino[5,6-b]indole-3-carboxamide-1,1-dioxide; M.p.: 252° C. (decomposition).

EXAMPLE 25

2,5-Dihydro-2,5-dimethyl-4-hydroxy-8-methoxy-N-phenyl-1,2-thiazino[5,6-b]indole-3-carboxamide-1,1-dioxde was prepared analogous to Example 23 from methyl 2,5-dihydro-2,5-dimethyl-4-hydroxy-8-methoxy-1,2-thiazino[5,6-b]indole-3-carboxylate 1,1-dioxide and aniline with a yield of 78% of theory; M.p.: 246°–247° C. (decomposition).

EXAMPLE 26

2,5-Dihyro-4-hydroxy-N-(2-thiazolyl)-2,5,8-trimethyl-1,2-thiazino[5,6-b]indole-3-carboxamide-1,1-dioxide by method A 1.5 gm (4.5 millimols) of methyl 2,5-dihydro-4-hydroxy-2,5,8-trimethyl-1,2-thiazino[5,6-b]indole-3-carboxylate 1,1-dioxide, 0.5 gm (5 millimols) of 2-aminothiazole and 0.1 gm of tri-n-butyl borate were refluxed in 180 ml of xylene for 6 hours. After cooling, the crystals which had formed were filtered off and recrystallized from ethylene chloride/ethanol. Yield: 0.7 gm (38% of theory) of 2,5-dihydro-4-hydroxy-N-(2-thiazolyl)-2,5,8-trimethyl-1,2-thiazino[5,6-b]indole-3-carboxamide-1,1-dioxde; M.p.: 265° C. (decomposition).

Elemental analysis: $C_{17}H_{16}N_4O_4S_2$ (404.48): Calc.: C-50.48%; H-3.99%; N-13.85%; S-15.86%: Found: C-50.30%; H-3.96%; N-13.84%; S-15.75%.

The starting compound was obtained by the following reaction sequence:

(a) 6.6 gm (33 millimols) of ethyl 5-methyl-indole-2-carboxylate were reacted analogous to Example 18(a) with 1.6 gm of a 55% solution of sodium hydride in oil (36 millimols) and 4.7 gm (33 millimols) of methyl iodide in hexamethylphosphoric acid triamide to yield, after recrystallization from ethanol, 4.0 gm (56% of theory) of ethyl 1,5 dimethyl-indole-2-carboxylate; M.p.: 50°–52° C.

(b) 10.0 gm (51 millimols) of ethyl 1,5-dimethyl-indole-2-carboxylate were reacted analogous to Example 18(b) with 28 ml of thionyl chloride, and the thus obtained yellow crystals (ethyl 3-chloro-sulfinyl-1,5-dimethyl-indole-2-carboxylate) was reacted with a solution of ammonia in ether at −70° C. to yield 8.8 gm (61% of theory) of ethyl 3-aminosulfinyl-1,5-dimethyl-indole-2-carboxylate; M.p.: 118° C.

(c) 8.0 gm (29 millimols) of ethyl 3-aminosulfinyl-1,5-dimethyl-indole-2-carboxylate were reacted analogous to Example 18(c) with 3.0 gm (19 millimols) of sodium permanganate to yield b 5.9 gm (70% of theory) of ethyl 1,5-dimethyl-3-sulfamoyl-indole-2-carboxylate, M.p.: 148° C., and 2.0 gm (28% of theory) of 4,7-dimethyl-2H-isothiazolo[4,5-b]indole-3(2H)-one-1,1-dioxide; M.p.: 295° C. (decompositon).

By heating with one equivalent of sodium methylate in ethanol and subsequent acidification, ethyl 1,5-dimethyl-3-sulfamoyl-indole-2-carboxylate was converted into 4,7-dimethyl-2H-isothiazolo[4,5-b]indole-3(2H)-one-1,1-dioxide.

(d) 3.0 gm (27.5 millimols) of methyl chloroacetate were added to a solution of 1.35 gm (25 millimols) of sodium methylate and 6.9 gm (23 millimols) of 4,7-dimethyl-2H-isothiazolo[4,5-b]indole-3(2H)-one-1,1-dioxide in 15 ml of anhydrous dimethylsulfoxide. The reaction mixture was then heated for one hour at 130° C. and, after cooling, was stirred into a solution of 2.5 gm of sodium acetate in 40 ml of water. The precipitate formed thereby was washed with ice water, dried and recyrstallized to yield 3.6 gm (48% of theory) of methyl 3,4-dihydro-4,7-dimethyl-3-oxo-2H-isothiazolo[4,5-b]indole-2-acetate 1,1-dioxide; M.p.: 248° C.

(e) 4.0 gm of methyl, 3,4-dihydro-4,7-dimethyl-3-oxo-2-H-isothiazolo[4,5-b]-indole-2-acetate 1,1-dioxide were reacted analogous to Example 18(e) with 2.0 gm of sodium methylate in toluene/tert. butanol to yield, after further processing and recrystallization from ethylene chloride/methanol, 2.0 gm (50% of theory) of methyl 2,5-dihydro-5,8-dimethyl-4-hydroxy-1,2-thiazino[5,6-b]indole-3-carboxylate 1,1-dioxde; M.p.: 260° C. (decomposition).

(f) 1.7 gm of methyl 2,5-dihydro-5,8-dimethyl-4-hydroxy-1,2-thiazino[5,6-b]indole-3-carboxylate-1,1-dioxide were reacted analogous to Example 18(f) with 5.3 ml of 1 N sodium hydroxide and 2.6 gm of methyl iodide in 20 ml of methanol to yield 1.5 gm (84% of theory) of methyl 2,5-dihydro-4-hydroxy-2,5,8-trimethyl-1,2-thiazino [5,6-b]indole-3-carboxylate-1,1-dioxide; M.p.: 144°–145° C.

EXAMPLE 27

Methyl 2,5-dihydro-4-hydroxy-2,5,8-trimethyl-1,2-thiazino [5,6-b[indole-3-carboylate-1,1-dioxide was reacted with 2-amino-4-methyl-thiazole analogous to Example 26 to give 2,5-dihydro-4-hydroxy-N-(4-methyl-2-thiazolyl)-2,5,8-trimethyl-1,2-thiazino[5,6-b]indole-3-carboxamide-1,1-dioxide. Yield: 52% of theory.

EXAMPLE 28

Analogous to Example 26, the following compounds were prepared from (a) methyl 8-ethyl-2,5-dihydro-2,5-dimethyl-4-hydroxy-1,2-thiazino[5,6-b]indole-3-caboxylate-1,1-dioxide, (b) methyl 2,5-dihydro-2,5-dimethyl-4-hydroxy-7-trifluoro-methyl-1,2-thiazino[5,6-b]indole-3-carboxylate-1,1-dioxde, and (c) methyl 2,5-dihydro-4-hydroxy-2,5,7-trimethyl-1,2-thiazino[5,6-b]indole-3-carboxylate-1,1-dioxide, respectively, and 2-amino-thiazole:

(a) 8-Ethyl-2,5-dihydro-2,5-dimethyl-4-hydroxy-N-(2-thiazolyl)-1,2-thiazino[5,6-b]indole-3-carboxamide-1,1-dioxide; Yield: 61% of theory;

(b) 2,5-Dihydro-2,5-dimethyl-4-hydroxy-N-(2-thiazolyl)-7-trifluoromethyl-1,2-thiazino[5,6-b]indole-3-carboxamide-1,1-dioxide; Yield: 47% of theory;

(c) 2,5-Dihydro-4-hydroxy-N-(2-thiazolyl)-2,5,7-trimethyl-1,2-thiazino[5,6-b]indole-3-carboxamide-1,1-dioxide; Yield: 58% of theory.

The starting compounds were obtained from (a) ethyl 5-ethyl-indole-2-carboxylate, (b) ethyl 6-trifluoromethyl-indole-2-carboxylate, and (c) ethyl 6-methyl-indole-2-carboxylate, respectively, by subsequent reactions with methyl iodide analogous to Example 26(a), with thionylchloride and ammonia analogous to Example 26(b), with potassium permanganate analogous to Example 26(c), with sodium methylate and methyl chloroacetate analogous to Example 26(d) and finally by treatment with sodium methylate analogous to Example 26(e) and with methyl iodide analogous to Example 26(f).

EXAMPLE 29

2,5-Dihydro-2,5-dimethyl-4-hydroxy-N-phenyl-1,2-thiazino [5,6-b]-indole-3-carboxamide-1,1-dioxide was prepared analogous to Example 9 from methyl 2,5-dihydro-2,5-dimethyl-4-hydroxy-1,2-thiazino[5,6-b]indole-3-carboxylate-1,1-dioxide and aniline in toluene; M.p.: 269°–270° C. (decomposition);

$C_{19}H_{17}N_3O_4S$ (383,43): Calc.: C-59.52%; H-44.47%; N-10.96%; S-8.36%: Found: C-59.50%; H-44.56%; N-10.71%; S-8.37%.

EXAMPLE 30

2,5-Dihydro-2,5-dimethyl-N-(4-fluoro-phenyl)-4-hydroxy-1,2-thiazino[5,6-b]indole-3-carboxamide-1,1-dioxide was prepared analogous to Example 9 from n-butyl 2,5-dihydro-2,5-dimethyl-4-hydroxy-1,2-thiazino[5,6-b]indole-3-carboxylate-1,1-dioxide and 4-fluoro-aniline in xylene; M.p.: 271°–272° C. (decomp.); Yield: 68% of theory;

Elemental analysis: $C_{19}H_{16}FN_3O_4S$ (401.42):

Calc.: C-56.86%; H-4.02%; N-10.47%; S-7.99%: Found: C-56.90%; H-3.97%; N-10.78%; S-8.31%.

The starting compound, n-butyl 2,5-dihydro-2,5-dimethyl-4-hydroxy-1,2-thiazino[5,6-b]indole-3-carboxylate-1,1-dioxide, M.p.: 143°–145° C. (from xylene), was prepared from methyl 2,5-dihydro-2,5-dimethyl-4-hydroxy-1,2-thiazino-[5,6-b]indole-3-carboxylate-1,1-dioxide and n-butanol in xylene; Yield: 73% of theory.

Elemental analysis: $C_{17}H_{20}N_2O_5S$ (364.43): Calc.: C-56.02%; H-5.53%; N-7.69%; S-8.80%: Found: C-55.90%; H-5.53%; N-7.69%; S-9.00%.

EXAMPLE 31

2,5-Dihydro-2,5-dimethyl-4-hydroxy-N-(4-methyl-2-thiazolyl)-1,2-thiazino[5,6-b]indole-3-carboxamide-1,1-dioxide was prepared analogous to Example 2 from benzyl 2,5-dihydro-2,5-dimethyl-4-hydroxy-1,2-thiazino[5,6-b]indole-3-carboxylate-1,1-dioxide and 2-amino-4-methyl-thiazole in xylene; M.p.: 270° C. (decomp.); Yield: 67% of theory;

Elemental analysis: $C_{17}H_{16}N_4O_4S_2$ (404.47): Calc.: C-50.48%; H-3.99%; N-13.85%; S-15.85%: Found: C-50.50%; H-3.81%; N-13.88%; S-15.61%.

The starting compound, benzyl 2,5-dihydro-2,5-dimethyl-4-hydroxy-1,2-thiazino[5,6-b]indole-3-carboxylate-1,1-dioxide, M.p.: 208°–209° C., was prepared from methyl 2,5-dihydro-2,5-dimethyl-4-hydroxyl-1,2-thiazino-[5,6-b]indole-3-carboxylate-1,1-dioxide and benzyl alcohol in xylene; Yield: 84% of theory.

Elemental analysis: $C_{20}H_{18}N_2O_5S$ (398.45): Calc.: C-60.29%; H-4.55%; N-7.03%; S-8.05%: Found: C-60.10%; H-4.58%; N-6.93%; S-7.94%.

EXAMPLE 32

2,5-Dihydro-2,5-dimethyl-4-hydroxy-N-(2-thiazolyl)-1,2-thiazino-[5,6-b]indole-3-carboxamide-1,1-dioxide by method A 0.32 gm (1.0 millimol) of phenyl 2,5-dihydro-2,5-dimethyl-4-hydroxy-1,2-thiazino[5,6-b]indole-3-carboxylate-1,1-dioxide and 0.12 gm (1.2 millimols) of 2-amino-thiazole were refluxed in 30 ml of xylene for 1 hour. After cooling and standing overnight, the crystals which had formed were suction-filtered off and washed with ether. Yield: 0.35 gm (90% of theory); M.p.: 260°–261° C. (decomposition).

Elemental analysis: $C_{16}H_{14}N_4O_4S_2$ (390.44): Calc.: C-49.22%; H-3.55%; N-14.42%; S-16.43%: Found: C-49.30%; H-3.51%; N-14.57%; S-16.31%.

The starting compound, phenyl 2,5-dihydro-2,5-dimethyl-4-hydroxy-1,2-thiazino[5,6-b]indole-3-carboxylate-1,1-dioxide, M.p.: 262°–264° C. (decomp.), was prepared from methyl 2,5-dihydro-2,5-dimethyl-4-hydroxy-1,2-thiazino [5,6-b]indole-3-carboxylate-1,1- dioxide and an excess of phenol in xylene; Yield: 51% of theory.

Elemental analysis: $C_{19}H_{16}N_2O_5S$ (384.42): Calc.: C-59.36%; H-4.20%; N-7.29%; S-8.34%: Found: C-59.30%; H-4.15%; N-7.23%; S-8.45%.

EXAMPLE 33

2,5-Dihydro-2,5-dimethyl-4-hydroxy-N-phenyl-1,2-thiazino [5,6-b]indole-3-carboxamide-1,1-dioxide by method B 1.3 gm (9 millimols) of methyl iodide were added to a solution of 1.0 gms (2.7 millimols) of 2,5-dihydro-4-hydroxy-5-methyl-N-phenyl-1,2-thiazino[5,6-b]indole-3-carboxamide-1,1-dioxide in 30 ml of methanol and 2.7 ml of 1 N sodium hydroxide. The reaction mixture was then stirred for 6 hours at room temperature and then neutralized. The precipitate formed thereby was filtered off, washed with water and recrystallized from xylene. Yield: 750 mgm (73% of theory) of 2,5-dihydro-2,5-dimethyl-4-hydroxy-N-phenyl-1,2-thiazino[5,6-b]indole-3-carboxamide-1,1-dioxide; M.p.: 269°-270° C. (decomposition);

Elemental analysis: $C_{19}H_{17}N_3O_4S$ (383.43): Calc.: C-59.52%; H-4.47%; N-10.96%; S-8.36%: Found: C-59.50%; H-4.58%; N-10.81%; S-8.44%.

EXAMPLE 34

Analogous to Example 33, the following compounds were prepared from (a) 2,5-dihydro-4-hydroxy-5-methyl-N-(2-thiazolyl)-1,2-thiazino-[5,6-b]indole-3-carboxamide-1,1-dioxide, (b) 2,5-dihydro-4-hydroxy-5-methyl-N-(4-methyl-N-(4-methyl-2-thiazolyl)-1,2-thiazino[5,6-b]indole-3-carboxamide-1,1-dioxide, (c) 2,5-dihydro-N-(4,5-dimethyl-2-thiazolyl) 4-hydroxy-5-methyl-1,2-thiazino[5,6-b]indole-3-carboxamide-1,1-dioxide, (d) 2,5-dihydro-4-hydroxy-5-methyl-N-(2-pyridyl)-1,2-thiazino[5,6-b-indole-3-carboxamide-1,1-dioxide, and (e) 2,4-dihydro-4-hydroxy-5-methyl-N-(6-methyl-2-pyridyl)-1,2-thiazino[5,6-b]indole-3-carboxamide-1,1-dioxide, respectively, and methyl iodide:
(a) 2,5-Dihydro-2,5-dimethyl-4-hydroxy-N-(2-thiazolyl)-1,2-thiazino[5,6-b]indole-3-carboxamide-1,1-dioxide; Yield: 18% of theory; M.p.: 260°-261° C. (decomposition);
(b) 2,5-Dihydro-2,5-dimethyl-4-hydroxy-N-(4-methyl-2-thiazolyl)-1,2-thiazino[5,6-b]indole-3-carboxamide-1,1-dioxide; Yield: 27% of theory; M.p.: 270° C. (decomposition);
(c) 2,5-Dihydro-2,5-dimethyl-N-(4,5-dimethyl-2-thiazolyl)-4-hydroxy-1,2-thiazino[5,6-b]indole-3-carboxamide-1,1-dioxide; Yield: 22% of theory; M.p.: 265° C. (decomposition);
(d) 2,5-Dihydro-2,5-dimethyl-4-hydroxy-N-(2-pyridyl)-1,2-thiazino-[5,6-b]indole-3-carboxamide-1,1-dioxide; Yield: 31% of theory; M.p. 232°-233° C. (decomposition);
(e) 2,5-Dihydro-2,5-dimethyl-4-hydroxy-N-(6-methyl-2-pyridyl)-1,2-thiazino[5,6-b]indole-3-carboxamide-1,1-dioxide; Yield: 25% of theory; M.p.: 229° C. (decomposition);

The same results and the same yields were obtained by using methyl bromide instead of methyl iodide.

EXAMPLE 35

2,5-Dihydro-2,5-dimethyl-4-hydroxy-N-phenyl-1,2-thiazino[5,6-b]-indole-3-carboxamide-1,1-dioxide by method C A solution of 1.0 gm (3.7 millimols) of 2,5-dihydro-2,5-dimethyl-1,2-thiazino[5,6-b]indole-4(3H)-one-1,1-dioxide and 0.44 ml (4.0 millimols) of phenyl isocyanate in 20 ml of dimethylformamide was added to a suspension of 230 mgm of a 55% sodium hydride-in-oil dispersion (5.0 millimols) in 15 ml of dimethylformamide, while cooling on ice. The reaction mixture was stirred for 30 min. on an ice bath and then for 4 hours at room temperature. Afterwards, it was stirred into 100 ml of aqueous 3 N hydrochloric acid. The precipitate formed thereby was filtered off, washed with water, dried and recrystallized from xylene, yielding 340 mgm (27% of theory) of 2,5-dihydro-2,5-dimethyl-4-hydroxy-N-phenyl-1,2-thiazino[5,6-b]indole-3-carboxamide-1,1-dioxide; M.p.: 269°-270° C. (decomposition).

Elemental analysis: $C_{19}H_{17}N_3O_4S$ (383.43): Calc.: C-59.52%; N-4.47%; N-10.96%; S-8.36%: Found: C-59.40%; H-4.57%; N-10.99%; S-8.31%.

The starting compound was prepared by the following reaction sequence:
(a) 50 ml of dimethylsulfoxide were added to a mixture of 2.4 gm (45 millimols) of sodium methylate and 10 gm (42 millimols) of 4-methyl-2H-isothiazolo[4,5-b]indole-3(4H)-one-1,1-dioxide, while cooling. After one hour of stirring at room temperature, 4.6 gm (50 millimols) of chloroacetone were added. The reaction mixture was heated for 2.5 hours on an oil bath at 125° C. and, after cooling, a solution of 15 gm of sodium acetate in 400 ml of water was added. The precipitate formed thereby was filtered off, washed with water, ice-cold methanol and ether, and dried. Yield: 8.3 gm (68% of theory) of 2-acetonyl-4-methyl-2H-isothiazolo[4,5-b]indole-3(4H)-one-1,1-dioxide; M.p.: 188°-189° C. (from ethylene chloride).
(b) 10 gm (34 millimols) of 2-acetonyl-4-methyl-2H-isothiazolo [4,5-b]-indole-3(4H)-one-1,1-dioxide were added to a methanolic sodium methylate solution [1.6 gm of sodium (0.107 gm-atoms) in 60 ml of anhydrous methanol]. After half an hour of stirring at room temperature, the mixture was heated for 45 minutes on an oil bath at 60° C. Subsequently, the reaction mixture was cooled on an ice bath and acidified with 1 N hydrochloric acid to a pH of 3-4. The precipitate formed thereby was filtered off, washed with ice water, dried and recrystallized from ethylene chloride, yielding 6.4 gm (64% of theory) of 3-acetyl-2,5-dihydro-4-hydroxy-5-methyl-1,2-thiazino[5,6-b ]-indole-1,1-dioxide. M.p.: 210°-211° C.;

Elemental analysis: $C_{13}H_{12}N_2O_4S$ (292.32): Calc.: C-53.42%; H-4.14%; N-9.58%; S-10.97%: Found: C-53.60%; H-4.07%; N-9.58%; S-10.63%.
(c) 6.2 gm (21.2 millimols) of 3-acetyl-2,5-dihydro-4-hydroxy-5-methyl-1,2-thiazino[5,6-b]indole-1,1-dioxide, 12.4 gm (0.2 mol) of freshly distilled glycol and 0.5 gm of p-toluenesulfonic acid were refluxed in 300 ml of benzene for 120 hours in a vessel equipped with a water trap. After addition of another 300 ml of benzene, the reaction mixture was washed with an aqueous sodium bicarbonate solution until neutral, treated with activated charcoal, dried with magnesium sulfate, and evaporated to a volume of about 30 ml. 2.9 gm (47% of theory) of 2,5-dihydro-5-methyl-1,2-thiazino[5,6-b]indole-4(3H)-one-1,1-dioxide ethylene ketal cristallized out; M.p.: 205°-206° C. (from benzene).
(d) A mixture of 2.7 gm (9.2 millimols) of 2,5-dihydro-5-methyl-1,2-thiazino[5,6-b]indole-4(3H)-one-1,1-dioxide ethylene ketal and a suspension of 1.92 gm (13.5 millimols) of methyl iodide in 30 ml of isopropanol and 10 ml of water was admixed with 9.7 ml of 1 N sodium hydroxide (9.7 millimols). After stirring the mixture for 24 hours at room temperature, the precipitate which had formed was suction-filtered off, washed with water and ice-cold isopropanol, and recrystallized from ethanol. Yield: 2.4 gm (88% of theory) of 2,5-dihydro-2,5-dimethyl-1,2-thiazino[5,6-b]indole 4(3H)-one-1,1-dioxide-ethylene ketal; M.p.: 184° C.

(e) 2.2 gm (7.4 millimols) of 2,5-dihydro-2,5-dimethyl-1,2-thiazino[5,6-b]-indole-4(3H)-one-1,1-dioxide-ethylene ketal were refluxed for one hour in a mixture of 60 ml of 9% hydrochloric acid and 60 ml of methanol. Subsequently, the mixture was evaporated to dryness in vacuo. After taking up the residue in methylene chloride, washing the solution with water, drying and evaporating it, and recrystallizing the raw product from ethanol, 1.6 gm (82% of theory) of 2,5-dihydro-2,5-dimethyl-1,2-thiazino-[5,6-b]indole-4(3H)-one-1,1-dioxide were obtained; M.p.: 180° C.; $^1$H-NMR (CDCl$_3$): δ = 8.0 (m, 1) and 7.4 (m, 3; arom. H) 4.15 (s, 2, CH$_2$); 4.06 (s, 3, 5-CH$_3$); 3.00 (s, 3, 2-CH$_3$).

Elemental analysis: $C_{12}H_{12}N_2O_3S$ (264.31): Calc.: C-54.53%; H-4.57%; N-10.60%; S-12.13%: Found: C-54.30%; H-4.57%; N-10.65%; S-11.85%.

EXAMPLE 36

2,5-Dihydro-2,5-dimethyl-4-hydroxy-N-(2-thiazolyl)-1,2-thiazino-[5,6-b]indole-3-carboxamide-1,1-dioxide by method D 1 gm (2.6 millimols) of 2,5-dihydro-2,5-dimethyl-4-hydroxy-N-phenyl-1,2-thiazino[5,6-b]indole-3-carboxamide-1,1-dioxide was refluxed for 48 hours with 800 mgm (8 millimols) of 2-amino-thiazole, 0.1 gm of tri-n-butyl borate and 0.1 gm of p-toluenesulfonic acid in 250 ml of xylene. After cooling, the reaction mixture was filtered. The filter cake was used directly for the subsequent column-chromatographic separation, and the filtrate was extracted with 3 N aqueous hydrochloric acid, washed, dried and evaporated. The combined solids were column-chromatographically purified (Merck-silica gel 60, particle size: 0.2–0.5 mm; eluant: chloroform/ethanol, 9:1). Yield: 0.35 gm (34% of theory) of 2,5-dihydro-2,5-dimethyl-4-hydroxy-N-(2-thiazolyl)-1,2-thiazino[5,6-b]indole-3-carboxamide-1,1-dioxide; M.p.: 260°–261° C. (decomposition)

Elemental analysis: $C_{16}H_{14}N_4O_4S_2$ (390.44): Calc.: C-49.22%; H-3.55%; N-14.42%; S-16.43%: Found: C-49.00%; H-3.61%; N-14.30%; S-16.41%.

EXAMPLE 37

2,5-Dihydro-2,5-dimethyl-4-hydroxy-N-(2-thiazolyl)-1,2-thiazino-[5,6-b]indole-3-carboxamide-1,1-dioxide was prepared analogous to Example 36 from 2,5-dihydro-2,5-dimethyl-4-hydroxy-1,2-thiazino[5,6-b]indole-3-carboxamide-1,1-dioxide and 2-amino-thiazole with a yield of 46% of theory; M.p.: 260°–261° C. (decomp.).

The starting compound was prepared as follows:

(a) 3 gm (10.2 millimols) of methyl 2,5-dihydro-4-hydroxy-5-methyl-1,2-thiazino-[5,6-b]indole-3-carboxylate-1,1-dioxide were admixed with 150 ml of concentrated aqueous ammonia, and the mixture was stirred for 12 hours at room temperature. The reaction mixture was then evaporated in vacuo, and the residue was treated with ice water. The precipitate formed thereby was then suction-filtered off, washed with a small amount of ice water, and recrystallized several times from glacial acetic acid. Yield: 2,0 gm (70% of theory) of 2,5-dihydro-4-hydroxy-5-methyl-1,2-thiazino[5,6-b]indole-3-carboxamide-1,1-dioxide.

Elemental analysis: $C_{12}H_{11}N_3O_4S$ (293.31): Calc.: C-49.14%; H-3.78%; N-14.33%; S-10.93%: Found: C-49.30%; H-3.63%; N-14.17%; S-10.81%.

(b) 1.5 gm (5.1 millimols) of 2,5-dihydro-4-hydroxy-5-methyl-1,2-thiazino-[5,6-b]indole-3-carboxamide-1,1-dioxide and 0.7 gm (5 millimols) of methyl iodide were admixed with a solution of 0.27 gm (5 millimols) of sodium methylate in 20 ml of dimethylformamide, and the mixture was stirred for 20 hours at room temperature. Subsequently, the mixture was weakly acidified with 1 N hydrochloric acid, and the precipitate formed thereby was suction-filtered off and recrystallized from ethylene chloride/ethanol. Yield: 1.05 gm (67% of theory) of 2,5-dihydro-2,5-dimethyl-4-hydroxy-1,2-thiazino-[5,6-b]indole-3-carboxamide-1,1-dioxide.

Elemental analysis: $C_{13}H_{13}N_3O_4S$ (307.34): Calc.: C-50.81%; H-4.26%; N-13.67%; S-10.43%: Found: C-50.80%; H-4.25%; N-13.63%; S-10.37%.

EXAMPLE 38

2,5-Dihydro-2,5-dimethyl-4-hydroxy-N-(2-thiazolyl)-1,2-thiazino-[5,6-b]indole-3-carboxamide-1,1-dioxide was prepared analogous to Example 36 from N-(n-butyl)-2,5-dihydro-2,5-dimethyl-4-hydroxy-1,2-thiazino[5,6-b]indole-3-carboxamide-1,1-dioxide and 2-amino-thiazole with a yield of 37% of theory; M.p.: 260°–261° C. (decomp.)

The starting compound, N-(n-butyl)-2,5-dihydro-2,5-dimethyl-1,2-thiazino[5,6-b]indole-3-carboxamide-1,1-dioxide, was prepared analogous to Example 35 from 2,5-dihydro-2,5-dimethyl-1,2-thiazino[5,6-b]indole-4(3H)-one-1,1-dioxide and n-butyl isocyanate with a yield of 42% of theory.

Analogously, the following compounds were also prepared from N-(n-butyl)-2,5-dihydro-2,5-dimethyl-4-hydroxy-1,2-thiazino[5,6-b]indole-3-carboxamide-1,1-dioxide:

(a) 2,5-Dihydro-2,5-dimethyl-4-hydroxy-N-(4-methyl-2-thiazolyl)-1,2-thiazino[5,6-b]indole-3-carboxamide-1,1-dioxide, Yield: 33% of theory; M.p.: 270° C. (decomposition);

(b) 2,5-Dihydro-2,5-dimethyl-N-(4,5-dimethyl-2-thiazolyl)-4-hydroxy-1,2-thiazino[5,6-b]indole-3-carboxamide-1,1-dioxide, Yield: 37% of theory; M.p.: 265° C. (decomposition);

(c) 2,5-Dihydro-2,5-dimethyl-4-hydroxy-N-(2-pyridyl)-1,2-thiazino-[5,6-b]indole-3-carboxamide-1,1-dioxide, Yield: 30% of theory; M.p.: 232°–233° C. (decomposition);

(d) 2,5-Dihydro-2,5-dimethyl-4-hydroxy-N-(6-methyl-2-pyridyl)-1,2-thiazino[5,6-d]indole-3-carboxamide-1,1-dioxide, Yield: 28% of theory; M.p.: 229° C. (decomposition).

EXAMPLE 39

2,5-Dihydro-2,5-dimethyl-4-hydroxy-N-phenyl-1,2-thiazino[5,6-b]-indole-3-carboxamide-1,1-dioxide by method E A solution of 0.19 gm (2 millimols) of aniline in 5 ml of dry tetrahydrofuran was added dropwise at −40° C. to solution of 2,5-dihydro-2,5-dimethyl-4-(1-pyrrolidinyl)-1,2-thiazino[5,6-b]-indole-3-carboxylic acid chloride-1,1-dioxide in tetrahydrofuran, which was obtained by reacting 0.32 gm (1 millimols) of 2,5-dihydro-2,5-dimethyl-4-(1-pyrrolidinyl)-1,2-thiazino[5,6-b]indole-1,1-dioxide with 0.125 gm (1.25 millimols) of phosgene and 0.125 gm (1.25 millimols) of triethylamine in 10 ml of anhydrous tetrahydrofuran. The resulting mixture was allowed to warm to room temperature over a period of 6 hours, and was then stirred for 24 hours. Afterward, ice water was added to the mixture, and the aqueous mixture was extracted twice with methylene chloride. The combined organic phases were washed twice with water, dried over sodium sulfate and evaporated in vacuo. The residue, raw 2,5-dihydro-2,5-dimethyl-N-phenyl-4-(1-pyrrolidinyl)-1,2-thiazino[5,6-b]indole-3-carboxamide-1,1-dioxide, was dissolved in 6 ml of glacial acetic acid, and the solution was admixed with 2 ml of 2 N hydrochloric acid. The mixture was then warmed at 100° C. for 15 minutes and 50 ml of ice water were added after cooling. The mixture was then filtered, and the filter cake was dried and recrystallized from xylene. Yield: 185 mgm (48% of theory) of 2,5-dihydro-2,5-dimethyl-4-hydroxy-N-phenyl-1,2-thiazino[5,6-b]indole-3-carboxamide-1,1-dioxide; M.p.: 269°–279° C. (decomposition).

Elemental analysis: $C_{19}H_{17}N_3O_4S$ (383.43): Calc.: C-59.92%; H-4.47%; N-10.96%; S-8.36%: Found: C-59.80%; H-4.52%; N-10.90%; S-8.49%.

The starting compound was synthesized as follows:

(a) 2.64 gm (10 millimols) of 2,5-dihydro-2,5-dimethyl-1,2-thiazino[5,6-b]-indole-4(3H)-one-1,1-dioxide were heated with 1.0 gm (14 millimols) of freshly distilled pyrrolidine and 0.1 gm of p-toluenesulfonic acid in 200 ml of benzene for 96 hours in a vessel equipped with a water trap. After each 24 hours, equal amounts of pyrrolidine and p-toluene sulfonic acid were added to the mixture. The cooled reaction mixture was then admixed with ether and washed until neutral. The organic phase then was dried, evaporated and purified by recrystallization from ethanol. Yield: 1.4 gm (44% of theory) of 2,5-dihydro-2,5-dimethyl-4-(1-pyrrolidinyl)-1,2-thiazino[5,6-b]indole-1,1-dioxide; $^1$H-NMR (CDCl$_3$): δ = 8.00 (m, 1) and 7.4 (m, 3; arom. H); 6.05 (s, 1, 3-H); 4.10 (s, 3, 5-CH$_3$); 3.27 (s, 3,2-CH$_3$); 2.93 (m, 4, N-(CH$_2$)$_2$; 1.95 (m, 4, —(CH$_2$_)$_2$—).

Elemental analysis: $C_{16}H_{19}N_3O_2S$ (317.42): Calc.: C-60.54%; H-6.03%; N-13.42%; S-10.10%: Found: C-60.50%; H-6.18%; N-13.31%; S-10.17%.

(b) A solution of 0.32 gm (1 millimol) of 2,5-dihydro-2,5-dimethyl-4-(1-pyrrolidinyl)-1,2-thiazino[5,6-b]indole-1,1-dioxide and 0.125 gm (1.25 millimols) of triethylamine in 8 ml of anhydrous tetrahydrofuran at −40° C. was added to a solution of 0.125 gm (1.25 millimols) of phosgene (0.65 ml of a 20% solution in toluene were used) in 2 ml of anhydrous tetrahydrofuran. The reaction mixture was allowed to warm to room temperature over a period of one hour, and was allowed to stand for another 2 hours at room temperature. The enamine carboxylic acid chloride solution in tetrahydrofuran thus obtained was then used directly for the preparation of the desired end product.

EXAMPLE 40

Analogous to Example 39, the following compounds were prepared from 2,5-dihydro-2,5-dimethyl-4-(1-pyrrolidinyl)-1,2-thiazino[5,6-b]-indole-3-carboxylic acid-chloride-1,1-dioxide and (a) 2-amino-thiazole, (b) 2-amino-4-methyl-thiazole, (c) 2-amino-4,5-dimethyl-thiazole, (d) 2-amino-pyridine, and (e) 2-amino-6-methyl-pyrridine, respectively:

(a) 2,5-Dihydro-2,5-dimethyl-4-hydroxy-N-(2-thiazolyl)-1,2-thiazino-[5,6-b]indole-3-carboxamide-1,1-dioxide; Yield: 40% of theory; M.p.: 260°–261° C. (decomposition);

(b) 2,5-Dihydro-2,5-dimethyl-4-hydroxy-N-(4-methyl-2-thiazolyl)-1,2-thiazino[5,6-b]indole-3-carboxamide-1,1-dioxide; Yield: 36% of theory; M.p.: 270° C. (decomposition);

(c) 2,5-Dihydro-2,5-dimethyl-N-(4,5-dimethyl-2-thiazolyl)-4-hydroxy-1,2-thiazino[5,6-b]indole-3-carboxamide-1,1-dioxide; Yield: 33% of theory; M.p.: 265° C. (decomposition);

(d) 2,5-Dihydro-2,5-dimethyl-4-hydroxy-N-(2-pyridyl)-1,2-thiazino-[5,6-b]indole-3-carboxamide-1,1-dioxide;

(e) 2,5-Dihydro-2,5-dimethyl-4-hydroxy-N-(6-methyl-2-pyridyl)-1,2-thiazino[5,6-b]indole-3-carboxamide-1,1-dioxide; Yield: 28% of theory; M.p.: 229° C. (decomposition).

EXAMPLE 41

Sodium salt of 2,5-dihydro-2,5-dimethyl-4-hydroxy-N-(2-thiazolyl)-1,2-thiazino[5,6-b]indole-3-carboxamide-1,1-dioxide 0.064 mgm (1 millimol) of sodium methylate were added to a suspension of 0.39 gm (1 millimol) of 2,5-dihydro-2,5-dimethyl-4-hydroxy-N-(2-thiazolyl)-1,2-thiazino[5,6-b]indole-3-carboxamide-1,1-dioxide in 50 ml of methanol. The reaction mixture was then stirred for 24 hours at room temperature and afterwards concentrated by evaporation, and the residue was treated with isopropanol/ether. The crystals formed thereby were collected by suction filtration; Yield: 0.31 gm (75% of theory) of the sodium salt; M.p.: 265° C. (decomposition).

EXAMPLE 42

Cyclohexylamine salt of 2,5-dihydro-2,5-dimethyl-4-hydroxy-N-(4-methyl-2-thiazolyl)-1,2-thiazino[5,6-b]indole-3-carboxamide-1,1-dioxide 0.1 gm (1 millimol) of cyclohexylamine were added to a suspension of 0.4 gm (1 millimol) of 2,5-dihydro-2,5-dimethyl-4-hydroxy-N-(4-methyl-2-thiazolyl)-1,2-thiazino[5,6-b]indole-3-carboxamide-1,1-dioxide in 50 ml of methanol. The solution was then stirred at room temperature for 24 hours and afterwards evaporated in vacuo. The residue was treated with acetone/ether, suction-filtered, and the filter cake was washed with ether. Yield: 0.36 gm (72% of theory) of the cyclohexylamine salt. M.p.: 178° C. (decomposition).

Elemental analysis: $C_{23}H_{29}N_5O_4S_2$ (503.66): Calc.: C-54.85%; H-5.80%; N-13.91%; S-12.73%: Found: C-54.60%; H-6.02%; N-13.82%; S-12.91%.

EXAMPLE 43

2,5-Dihydro-2,5-dimethyl-4-hydroxy-N-(3-isothiazolyl)-1,2-thiazino[5,6-b]indole-3-carboxamide-1,1-dioxide by method A 1.0 gm (3.1 millimols) of methyl 2,5-dihydro-2,5-dimethyl-4-hydroxy-1,2-thiazino[5,6-b]indole-3-carboxylate-1,1-dioxide and 0.33 gm (3.3 millimols) of 3-amino-isothiazole were refluxed in 100 ml of xylene for 6 hours. The reaction mixture was then evaporated to a volume of about 10 ml, and the crystals formed thereby were suction-filtered off. Yield: 0.9 gm (74% of theory) of 2,5-dihydro-2,5-dimethyl-4-hydroxy-N-(3-isothiazolyl)-1,2-thiazino[5,6-b]indole-3-carboxamide-1,1-dioxide.

Elemental analysis: $C_{16}H_{14}N_4O_4S_2$ (390.44): Calc.: C-49.22%; H-3.55%; N-14.42%; S-16.43%: Found: C-49.30%; H-3.71%; N-14.30%; S-16.18%.

EXAMPLE 44

2,5-Dihydro-2,5-dimethyl-4-hydroxy-N-(5-methyl-3-isothiazolyl)-1,2-thiazino[5,6-b]indole-3-carboxamide-1,1-dioxide was prepared analogous to Example 43 from methyl 2,5-dihydro-2,5-dimethyl-4-hydroxy-1,2-thiazino[5,6-b]indole-3-carboxylate-1,1-dioxide and 2-amino-5-methyl-isothiazole with a yield of 82% of theory.

EXAMPLE 45

2,5-Dihydro-2,5-dimethyl-4-hydroxy-N-(3-hydroxy-2-pyridyl)-1,2-thiazino[5,6-b]indole-3-carboxylate 1,1-dioxide by method A 1.0 gm (3.1 millimols) of methyl 2,5-dihydro-2,5-dimethyl-4-hydroxy-1,2-thiazino[5,6-b]indole-3-carboxylate-1,1-dioxide and 0.36 gm (3.3 millimols) of 2-amino-3-hydroxypyridine were refluxed for 6.5 hours in 150 ml of xylene. The hot reaction mixture was then filtered, and the filter cake was washed and dried. Yield: 1.2 gm (97% of theory) of 2,5-dihydro-2,5-dimethyl-4-hydroxy-N-(3-hydroxy-2-pyridyl)-1,2-thiazino[5,6-b]indole-3-carboxamide-1,1-dioxide; M.p.: 225° C. (decomposition).

Elemental analysis: $C_{18}H_{16}N_4O_5S$ (400.42): Calc.: C-53.99%; H-4.03%; N-13.99%; S-8.01: Found: C-53.86%; H-4.92%; N-13.86%; S-7.90%.

EXAMPLE 46

2,5-Dihydro-2,5-dimethyl-4-hydroxy-N-(4-pyrimidinyl)-1,2-thiazino[5,6-b]indole-3-carboxamide-1,1-dioxide Analogous to Example 45, 0.7 gm (2.1 millimols) of methyl 2,5-dihydro-2,5-dimethyl-4-hydroxy-1,2-thiazino[5,6-b]indole-3-carboxylate-1,1-dioxide and 0.24 gm (2.5 millimols) of 4-amino-pyrimidine were reacted, yielding 0.7 gm (86% of theory) of 2,5-dihydro-2,5-dimethyl-4-hydroxy-N-(4-pyrimidinyl)-1,2-thiazino[5,6-b]indole-3-carboxamide-1,1-dioxide; M.p.: 255° C. (decomposition).

EXAMPLE 47

Analogous to Example 45, the following compounds were prepared from methyl 2,5-dihydro-2,5-dimethyl-4-hydroxy-1,2-thiazino[5,6-b]indole-3-carboxylate-1,1-dioxide and (a) 3-amino-pyridine, (b) 4-amino-pyridine, and (c) amino-pyrazine, respectively:
(a) 2,5-dihydro-2,5-dimethyl-4-hydroxy-N-(3-pyridyl)-1,2-thiazino[5,6-b]indole-3-carboxamide-1,1-dioxide; Yield: 76% of theory;
(b) 2,5-dihydro-2,5-dimethyl-4-hydroxy-N-(4-pyridyl)-1,2-thiazino[5,6-b]indole-3-carboxamide-1,1-dioxide; Yield: 83% of theory;
(c) 2,5-dihydro-2,5-dimethyl-4-hydroxy-N-pyrazinyl-1,2-thiazino[5,6-b]indole-3-carboxamide-1,1-dioxide; Yield: 91% of theory; M.p.: 252° C. (decomp.).

EXAMPLE 48

N-(2-benzimidazolyl)-2,5-dihydro-2,5-dimethyl-4-hydroxy-1,2 thiazino[5,6-b]indole-3-carboxamide-1,1-dioxide by method D 1.0 gm (3.1 millimols) of 2,5-dihydro-2,5-dimethyl-4-hydroxy-1,2-thiazino-[5,6-b]indole-3-carboxamide-1,1-dioxide and 0.41 gm (3.1 millimols) of 2-amino-benzimidazole were refluxed for 6 hours in 180 ml of xylene. The crystals which had formed in the hot solution were suction-filtered off, washed and dried. Yield: 1.1 gm (84% of theory) of N-(2-benzimidazolyl)-2,5-dihydro-2,5-dimethyl-4-hydroxy-1,2-thiazino-[5,6-b]indole-3-carboxamide-1,1-dioxide; M.p.: > 305° C.

EXAMPLE 49

2,5-Dihydro-2,5-dimethyl-4-hydroxy-N-(4-methyl-2-oxazolyl)-1,2-thiazino[5,6-b]indole-3-carboxamide-1,1-dioxide by method A 3.0 gm (9.1 millimols) of methyl 2,5-dihydro-2,5-dimethyl-4-hydroxy-1,2-thiazino-[5,6-b]indole-3-carboxylate-1,1-dioxide and 0.98 gm (10 millimols) of 2-amino-4-methyloxazole were refluxed for 4 hours in 250 ml of xylene. Upon cooling, the raw product crystallized out. Recrystallization from ethanol yielded 0.7 gm (20% of theory) of 2,5-dihydro-2,5-dimethyl-4-hydroxy-N-(4-methyl-2-oxazolyl)-1,2-thiazino[5,6-b]-indole-3-carboxamide-1,1-dioxide; M.p.: 128° C.

Elemental analysis: $C_{17}H_{16}N_4O_5S$ (388.42): Calc.: C-52.57%; H-4.15%; N-14.43%; S-8.26%: Found: C-52.80%; H-4.20%; N-14.20%; S-8.45%.

EXAMPLE 50

Analogous to Example 49, the following compounds were prepared from methyl 2,5-dihydro-2,5-dimethyl-4-hydroxy-1,2-thiazino[5,6-b]-indole-3-carboxylate-1,1-dioxide and (a) 2-amino-oxazole, (b) 2-amino-5-methyl-oxazole, and (c) 2-amino-benzoxazole, respectively:
(a) 2,5-Dihydro-2,5-dimethyl-4-hydroxy-N-(2-oxazolyl)-1,2-thiazino[5,6-b]indole-3-carboxamide-1,1-dioxide; Yield: 26% of theory;
(b) 2,5-Dihydro-2,5-dimethyl-4-hydroxy-N-(5-methyl-2-oxazolyl)-1,2-thiazino[5,6-b]indole-3-carboxamide-1,1-dioxide; Yield: 36% of theory;
(c) N-(2-benzisoxazolyl)-2,5-dihydro-2,5-dimethyl-4-hydroxy-1,2-thiazino[5,6-b]indole-3-carboxamide-1,1-dioxide; Yield: 56% of theory; M.p.: 246° C. (decomposition).

The compounds of the present invention, that is, those embraced by formula I and their non-toxic, pharmacologically acceptable salts formed with inorganic or organic bases, have useful pharmacodynamic properties. More particularly, they exhibit antiphlogistic activity and inhibit blood platelet aggregation in warm-blooded aminals, such as rats.

The blood platelet aggregation inhibiting activity and the toxicity of the compounds of this invention were ascertained by the test methods described below, and the tables show the results obtained for a few representative species, where A = 2,5-Dihydro-2,5-dimethyl-4-hydroxy-N-(2-thiazolyl)-1,2-thiazino[5,6-b]indole-3-carboxamide-1,1-dioxide
B = 2,5-Dihydro-2,5-dimethyl-4-hydroxy-N-(4-methyl-2-thiazolyl)-1,2-thiazino[5,6-b]indole-3-carboxamide-1,1-dioxide
C = 2,5-Dihydro-2,5-dimethyl-N-(4,5-dimethyl-2-thiazolyl)-4-hydroxy-1,2-thiazino[5,6-b]indole-3-carboxamide-1,1-dioxide
D = 2,5-Dihydro-2,5-dimethyl-4-hydroxy-N-(6-methyl-2-pyridyl)-1,2-thiazino[5,6-b]indole-3-carboxamide-1,1-dioxide
E = 8-Chloro-2,5-dihydro-2,5-dimethyl-4-hydroxy-N-(2-thiazolyl)-1,2-thiazino[5,6-b]indole-3-carboxamide-1,1-dioxide F = 2,5-Dihydro-2,5-dimethyl-4-hydroxy-8-methoxy-N-(2-pyridyl)-1,2-thiazino[5,6-b]indole-3-carboxamide-1,1-dioxide (a) BORN-Test, Collagen-Induced Aggregation The platelet aggregation was measured according to the method of BORN and CROSS (J. Physiol. 170, pp. 397 [1964]) in platelet-enriched plasma of healthy humans. The decrease in the optical density of the platelet suspension after addition of collagen was measured and registered photometrically. From the angle of inclination of the density curve the rate of aggregation can be determined. The point in the graph which showed the greatest light transmission, served for the measurement of the optical density. The quantity of collagen was chosen so that it produced an irreversible control curve.

The indicated values refer to the optical density and signify the percentage change in the light transmission (=% decrease in aggregation) under the influence of the test compound in comparision to the control.

Commercial collagen manufactured by Hormon-Chemie, Munich, Germany, was used.

The following table shows the results obtained from this test:

Table 1

| Compound | Concentration [Mol/liter] | BORN-Test [ = % decrease in aggregation] |
|---|---|---|
| A | $2 \times 10^{-5}$ | 96% |
|   | $2 \times 10^{-6}$ | 81% |
| B | $2 \times 10^{-5}$ | 100% |
|   | $2 \times 10^{-6}$ | 97% |
|   | $2 \times 10^{-7}$ | 42% |
| C | $2 \times 10^{-5}$ | 89% |
|   | $2 \times 10^{-6}$ | 82% |
| D | $5 \times 10^{-5}$ | 86% |
|   | $5 \times 10^{-6}$ | 60% |
| E | $1 \times 10^{-4}$ | 100% |
|   | $1 \times 10^{-5}$ | 86% |
|   | $1 \times 10^{-6}$ | 27% |
| F | $1 \times 10^{-4}$ | 85% |
|   | $1 \times 10^{-5}$ | 43% |

(b) Determination of Acute Toxicity

The acute toxicity was determined in male and female mice after oral administration of the test compound as a suspension in tylose.

The following table shows the animals which died within 1, 7 and 14 days after administration of the stated dosages.

Table 2

| Compound | Dosage [mgm/kg] | Number of animals | Dead animals within observation period | | |
|---|---|---|---|---|---|
| | | | 1 day | 7 days | 14 days |
| A | 1 000 | 10 | 0 | 0 | 0 |
| B | 1 000 | 10 | 0 | 0 | 0 |
| D | 1 000 | 10 | 0 | 0 | 0 |
| E | 1 000 | 10 | 0 | 0 | 0 |

The results tabulated above show that the compounds of the instant invention are very effective antithrombotics with practically negligible toxicity.

For pharmaceutical purposes the compounds of the present invention are administered to warm-blooded animals orally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like.

One effective dosage unit of the compounds according to the present invention is from 0.16 to 4.17 mgm/kg body weight, preferably 0.42 to 1.67 mgm/kg body weight. The daily dose rate is from 0.42 to 8.33 mgm/kg, preferably 0.83 to 4.2 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 51

Tablets

The tablet composition is compounded from the following ingredients:

| | |
|---|---|
| 2,5-Dihydro-2,5-dimethyl-4-hydroxy-N-(2-thiazolyl)-1,2-thiazine[5,6-b]indole-3-carboxamide-1,1-dioxide | 25.0 parts |
| Corn starch | 97.0 parts |
| Polyvinylpyrrolidone | 175.0 parts |
| Magnesium stearate | 3.0 parts |
| Total | 300.0 parts |

Preparation

A mixture of the active ingredient and the corn starch is moistened with an aqueous 14% solution of the polyvinylpyrrolidone and passed through a 1.5 mm-mesh screen. The granulate thus obtained is dried at 45° C. and passed once more through the said screen. The dry granulate is admixed with the magnesium stearate, and the composition is compressed into 300 mgm-tablets. Each tablet contained 25 mgm of the active ingredient and is an oral dosage unit composition.

EXAMPLE 52

Coated pills

The pill core composition is compounded from the following ingredients:

| | |
|---|---|
| 2,5-Dihydro-2,5-dimethyl-4-hydroxy-N-(2-thiazolyl)-1,2-thiazino[5,6-b]-indole-3-carboxamide-1,1-dioxide | 25.0 parts |
| Corn starch | 205.0 parts |
| Gelatin | 8.0 parts |
| Talcum | 18.0 parts |
| Magnesium stearate | 44.0 parts |
| Total | 300.0 parts |

Preparation

A mixture of the active ingredient and the corn starch is moistened with an aqueous 10% solution of the gelatin and passed through a 1.5 mm-mesh screen. The granulate thus obtained is dried at 45° C., again passed through the screen, the dry granulate is admixed with the talcum and the magnesium stearate, and the resulting composition is compressed into 300 mgm-pill cores, which are then coated with a thin shell consisting essentially of a mixture of talcum and sugar and finally polished with beeswax. Each coated pill contains 25 mgm of the active ingredient and is an oral dosage unit composition.

EXAMPLE 53

Gelatin capsules

The capsule filler composition is compounded from the following ingredients:

| | |
|---|---|
| 2,5-Dihydro-2,5-dimethyl-4-hydroxy-N-(2-thiazolyl)-1,2-thiazino[5,6-b]indole-3-carboxamide-1,1-dioxide | 25.0 parts |
| Corn starch | 365.0 parts |
| Colloidal silicic acid | 6.0 parts |
| Magnesium stearate | 4.0 parts |
| Total | 400.0 parts |

Preparation

The ingredients are intimately admixed with each other, and 400 mgm-portions of the composition are filled into gelatin capsules of suitable size. Each capsule contains 25 mgm of the active ingredient and is an oral dosage unit composition.

EXAMPLE 54

Suppositories

The suppository composition is compounded from the following ingredients:

| | |
|---|---|
| 2,5-Dihydro-2,5-dimethyl-4-hydroxy-N-(2-thiazolyl)-1,2-thiazino[5,6-b]indole 3-carboxamide-1,1-dioxide | 25.0 parts |
| Suppository base (e.g. cocoa butter) | 1725.0 parts |
| Total | 1750.0 parts |

Preparation

The pulverized active ingredient is stirred, by means of an immersion homogenizer, into the molten suppository base which has been cooled to 40° C., and 1750 mgm-portions of the mixture are poured into cooled suppository molds at 38° C. and allowed to harden therein. Each suppository contains 25 mgm of the active ingredient and is a rectal dosage unit composition.

EXAMPLE 55

Suspension

The suspension is compounded from the following ingredients:

| | | |
|---|---|---|
| 2,5-Dihydro-2,5-dimethyl-4-hydroxy-N-(2-thiazolyl)-1,2-thiazino[5,6-b]indole 3-carboxamide-1,1-dioxide | 0.5 | parts |
| Dioctyl sodium sulfosuccinate (DONSS) | 0.02 | parts |
| Benzoic acid | 0.1 | parts |
| Sodium cyclamate | 0.2 | parts |
| Colloidal silicic acid | 1.0 | parts |
| Polyvinylpyrrolidone | 0.1 | parts |
| Glycerin | 25.0 | parts |
| Grapefruit flavoring | 0.1 | parts |
| Distilled water q.s.ad | 100.0 | parts by vol. |

Preparation

The DONSS, the benzoic acid, the sodium cyclamate and the polyvinylpyrrolidone are dissolved in the distilled water at 70° C. The glycerin and silicic acid are then added. The resulting solution is cooled to room temperature, and the pulverized active ingredient is suspended therein by means of an immersion homogenizer. Subsequently, the flavoring is added, and the mixture is diluted with water to the indicated volume. 5 ml of the suspension contains 25 mgm of the active ingredient and is an oral dosage unit composition.

Any one of the other compounds embraced by formula I or a non-toxic salt thereof may be substituted for the particular active ingredient in Examples 51 through 55. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula wherein $R_1$ is hydrogen, methyl or ethyl;

$R_2$ is methyl or ethyl;

Y is hydrogen, fluorine, chlorine, bromine, methoxy, methyl, ethyl or trifluoromethyl; and Ar is 2-thiazolyl which may optionally have one or two methyl or ethyl substituents attached thereto; 5,6-dihydro-4H-cyclopentathiazol-2-yl; 4,5,6,7-tetrahydro-2-benzothiazolyl; 2-benzothiazolyl; 3-isothiazolyl which may optionally have a methyl substituent attached thereto; 2-pyridyl which may optionally have a methyl or hydroxyl substituent attached thereto; 3-pyridyl; 4-pyridyl; 4-pyrimidinyl; pyrazinyl; 2-benzimidazolyl 2-benzoxazolyl; 2-oxazolyl which may have a methyl substituent attached thereto; or phenyl which may optionally have a fluoro, chloro, bromo, methyl, ethyl, trifluoromethyl or methoxy substituent attached thereto; or a non-toxic, pharmaceutically acceptable salt thereof formed with an inorganic or organic base.

2. A compound of claim 1, which is 2,5-dihydro-2,5-dimethyl-4-hydroxy-N-(2-thiazolyl)-1,2-thiazino[5,6-b]-indole-3-carboxamide-1,1-dioxide or a non-toxic, pharmacologically acceptable salt thereof formed with an inorganic or organic base.

3. A compound of claim 1, which is 2,5-dihydro-2,5-dimethyl-4-hydroxy-N-(4-methyl-2-thiazolyl)-1,2-thiazino [5,6-b]indole-3-carboxamide-1,1-dioxide or a non-toxic pharmacologically acceptable salt thereof formed with an inorganic or organic base.

4. A compound of claim 1, which is 2,5-dihydro-2,5-dimethyl-N-(4,5-dimethyl-2-thiazolyl)-4-hydroxy-,1,2-thiazino[5,6-b]indole-3-carboxamide-1,1-dioxide or a non-toxic, pharmacologically acceptable salt thereof formed with an inorganic or organic base.

5. A compound of claim 1, whfich is 2,5-dihydro-2,5-dimethyl-4-hydroxy-N-(6-methyl-2-pyridyl)-1,2-thiazino [5,6-b]indole-3-carboxamide-1,1-dioxide or a non-toxic, pharmacologically acceptable salt thereof formed with an inorganic or organic base.

6. A compound of claim 1, which is 8-chloro-2,5-dihydro-2,5-dimethyl-4-hydroxy-N-(2-thiazolyl)-1,2-thiazino [5,6-b]indole-3-carboxamide-1,1-dioxide or a non-toxic, pharmacologically acceptable salt thereof formed with an inorganic or organic base.

7. A compound of claim 1, which is 2,5-dihydro-2,5-dimethyl-4-hydroxy-N-(2-pyridyl)-1,2-thiazino-[5,6-b]-indole-3-carboxamide-1,1-dioxide or a non-toxic, pharmacologically acceptable salt thereof formed with an inorganic or organic base.

8. An antiphlogistic or anthithrombotic pharmaceutical dosage unit composition consisting essentially of an inert pharmaceutical carrier and an effective antiphologistic or antithrombotic amount of a compound of claim 1.

9. The method of combatting inflammation or inhibiting blood platelet aggregation in a warm-blooded animal in need thereof, which comprises perorally, parenterally or rectally administering to said animal an effective antiphlogistic or antithrombotic amount of a compound of claim 1.

* * * * *